United States Patent
Bond et al.

(10) Patent No.: US 6,177,940 B1
(45) Date of Patent: *Jan. 23, 2001

(54) OUTCOMES PROFILE MANAGEMENT SYSTEM FOR EVALUATING TREATMENT EFFECTIVENESS

(75) Inventors: Malcolm L. Bond, Winters; Bruce Richard Chapman, Folsom, both of CA (US)

(73) Assignee: Cedaron Medical, Inc., Winters, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/530,939

(22) Filed: Sep. 20, 1995

(51) Int. Cl.[7] .............................. G06F 3/00; G06F 159/00
(52) U.S. Cl. .................................. 345/352; 705/3
(58) Field of Search ................... 395/352, 353, 395/354, 326, 961, 962, 968, 766, 768, 202, 203, 601, 769; 345/352, 353, 354, 326, 961, 962, 968; 707/505, 507, 508, 1; 705/2, 3, 10

(56) References Cited

U.S. PATENT DOCUMENTS

| | | | |
|---|---|---|---|
| 5,267,155 | * | 11/1993 | Buchanan et al. .................. 707/540 |
| 5,277,188 | * | 1/1994 | Selker .................................. 600/508 |
| 5,327,341 | * | 7/1994 | Whalen et al. ......................... 347/28 |
| 5,341,291 | * | 8/1994 | Roizen et al. ....................... 600/300 |
| 5,365,425 | * | 11/1994 | Torma et al. ............................. 705/2 |
| 5,557,514 | * | 9/1996 | Seare et al. .............................. 705/2 |
| 5,572,421 | * | 11/1996 | Altman et al. ........................... 705/3 |
| 5,583,758 | * | 12/1996 | McIlroy et al. .......................... 705/2 |
| 5,845,253 | * | 12/1998 | Rensimer et al. ....................... 705/2 |

OTHER PUBLICATIONS

Maitland, Murray E., et al., "A Client–Computer Interface for Questionnaire Data" *Arch. Phys.Med.Rehabil.* (Jun. 1994) vol. 75: 639–642.

Rozen, Michael F., et al., "Can Patients Use an Automated Questionnaire to Define Their Current Health Status?" *Medical Care* (May 1992) vol. 30: MS74–MS84.

* cited by examiner

*Primary Examiner*—Crescelle N. dela Torre
(74) *Attorney, Agent, or Firm*—Townsend and Townsend and Crew, LLP

(57) ABSTRACT

System for data input and storage and for correlation of such data against group data contained in a linked database. The data is input via a series of hierarchical menus, which menus may include sub-menus and fields that enable a user to directly input data for storage into the database. Data regarding an individual may be entered into the database directly by the individual using the hierarchical menu system.

22 Claims, 34 Drawing Sheets

Outcomes Report

Sort criteria

Referral Physician    Luciano Merlini

Total patients - 9
Number meeting sort criteria - 1

| | AVERAGE | N | Std Dev | Minimum | Maximum |
|---|---|---|---|---|---|
| Days from injury to first surgery | 367 | 1 | 0.0 | 367 | 367 |
| Days from initial rehabilitation to discharge | 153 | 1 | 0.0 | 153 | 153 |
| Days from injury to discharge | 427 | 1 | 0.0 | 427 | 427 |
| Number of visits | 2 | 1 | 0.0 | 2 | 2 |

*Fig. 8A*

Specify Group = male patients

Outcomes Report

| Referral Physician<br>Description of Symptoms | Alex Fanfani N | Alex Fanfani % | #1 N | #1 % | Jerry Balter N | Jerry Balter % | #2 N | #2 % | #3 N | #3 % | #4 N | #4 % |
|---|---|---|---|---|---|---|---|---|---|---|---|---|
| Wound, Scar | 0 | 0 | 0 | 0 | 0 | 0 | 0 | 0 | 0 | 0 | 0 | 0 |
| Edema, Inflammation | 0 | 0 | 0 | 0 | 0 | 0 | 0 | 0 | 0 | 0 | 0 | 0 |
| Vascular, Lymphatic | 0 | 0 | 0 | 0 | 0 | 0 | 0 | 0 | 0 | 0 | 0 | 0 |
| Pain, Hypersensitivity, Autonomic Ph | 0 | 0 | 0 | 0 | 0 | 0 | 0 | 0 | 0 | 0 | 0 | 0 |
| Nerve, Sensibility | 0 | 0 | 0 | 0 | 0 | 0 | 0 | 0 | 0 | 0 | 0 | 0 |
| Muscle, Myotendon unit, Tendon | 0 | 0 | 0 | 0 | 0 | 0 | 0 | 0 | 0 | 0 | 0 | 0 |
| Posture, Breathing patterns | 0 | 0 | 0 | 0 | 0 | 0 | 0 | 0 | 0 | 0 | 0 | 0 |
| ROM Deficiency | 0 | 0 | 0 | 0 | 0 | 0 | 0 | 0 | 1 | 100 | 0 | 0 |
| Praxis, Coordination | 0 | 0 | 0 | 0 | 0 | 0 | 0 | 0 | 0 | 0 | 0 | 0 |
| Strength, Endurance | 0 | 0 | 0 | 0 | 0 | 0 | 0 | 0 | 0 | 0 | 0 | 0 |
| Normal | 0 | 0 | 0 | 0 | 0 | 0 | 0 | 0 | 0 | 0 | 0 | 0 |
| Other | 0 | 0 | 0 | 0 | 0 | 0 | 0 | 0 | 0 | 0 | 0 | 0 |
| Total | 0 | | 0 | | 0 | | 0 | | 1 | 100 | 0 | |

1: Victor Duhowitz
2: Martha Robinson
3: Luciano Merlini
4: Alfred Margreth
More than 100% is possible due to multiple selections per patient
Primary Sort = symptoms
Report Breakdown = referral physicians

Primary Physician

1016

First Name: Luciano
Middle Initial
Last Name: Merlina ☒

Street: Via Cortina
City: Bologna

State: VE
Zip Code
Country: Italy

Day Phone: 51 423 1585
Evening Phone: 51 428 1754
Fax Phone: None

Alternate Contact

Social Security Number
Birth Date ← →
Gender: Male / Female

Select from List — 1017
Add to List
(ESC)
Clear Data
Revise List

During the past 4 weeks how often have you taken this medicine for your leg or foot pain?

Any medicine

- Never
- Occasionally
- Less than once a day
- Once a day
- More than once a day

*Fig. 18A*

During the past 4 weeks how often have you taken this medicine for your leg or foot pain?

Non prescription (Tylenol, Aspirin, Ibuprofen / Advil / Motrin)

- Never
- Occasionally
- Less than once a day
- Once a day
- More than once a day

*Fig. 18B*

Have you ever had any of the following conditions (indicate all that apply)?

- Diabetes
- Heart disease
- Stroke
- Arthritis other than in your back
- Asthma or other lung disease
- Depression
- High blood pressure (hypertension)
- Colitis
- Psoriasis

*Fig. 18C*

In the PAST WEEK, how often have you suffered:

weakness in arm and / or hand

- None of the time
- A little of the time
- Some of the time
- A good bit of the time
- Most of the time
- All the time

*Fig. 18D*

On a typical day during the PAST TWO WEEKS, have hand and wrist symtoms caused you to have any difficulty doing the following activity? Select the answer that best describes your ability to do the activity.

Writing

Left

No Difficulty

Mild Difficulty

Moderate Difficulty

Severe Difficulty

Cannot do at all due to hand or wrist symtoms

*Fig. 18E*

Refer to your symptoms in a typical 24 hour period during the PAST TWO WEEKS:

How severe is the hand or wrist pain you have at NIGHT?

Left

- I do not have hand or wrist pain at night
- Mild pain
- Moderate pain
- Severe pain
- Very severe pain

*Fig. 18F*

How satisfied are you with:
your treatment?

Very dissatisfied

Somewhat dissatisfied

Neutral

Somewhat satisfied

Very satisfied

*Fig. 18G*

Compression of a spinal nerve root confirmed by (i) specific imaging techniques -- CAT scan, myelography or MRI, or (ii) other diagnostic techniques (e.g. electromyography, venography)

No

Yes

*Fig. 18H*

OUTCOMES PROFILE MANAGEMENT SYSTEM FOR EVALUATING TREATMENT EFFECTIVENESS

TECHNICAL FIELD

The present invention relates generally to the field of report generation systems, and relates specifically to the field of menu-driven data entry and report generation systems which provide essentially real-time data analysis for comparing individual data points against a user-specified group to generate outcomes profile reports.

BACKGROUND

In today's changing, increasingly competitive health care environment, medical clinics are under new pressures to measure and control costs of delivered health care services. These new processes are loosely referred to as treatment outcome measurements. A component of this new era of outcomes measurement, or practice management, is the evaluation of a patient's perspective of the outcome of the delivered services.

In the new medical clinic setting, client satisfaction data is increasingly being considered as an important data point in deciding how to tune the delivery of a specific treatment plan. This client satisfaction information is collated with billing and resource utilization data to modify treatment plans to achieve optimal results with respect to goals of finance, clinic visits, and patient quality of life issues.

Conventional methods of collecting data relating to the health status and treatment satisfaction of an individual has been by using pen and pencil on a paper-based questionnaire. This method is time intensive for both the data collector and the individual, i.e., the health clinic staff data collector and the individual patient. Inputting such data into a database involves significant staff time and jeopardizes the integrity of the input data because human error is introduced during the transcription process. Some commercially available products have improved upon the pencil and paper approach and have sought to impact the speed of this data collection by using computerized forms and scanning the client responses into the computer (see, for example, DocuMed and OrthoGraphics). These currently commercially available methods and systems are time intensive for the individual and for the data collector. The scanning methods also jeopardize the integrity of the data because mistakes in interpretation by the scanning technology are common.

Direct individual-computer interactive programs have been researched with favorable results. The time taken by the data collector are significantly reduced and the integrity of the data generally is maintained. However, the methods employed by these approaches have required the individual to look at a question and then make a response by touching generically labelled control buttons. In addition, such an approach uses a small, dedicated liquid crystal display that is extremely difficult to read by the individual (see, Rozen et al., *Medical Care*, Vol. 30(5), pp. MS74–MS84, 1992).

Other methods and systems involve technology that displays the questions for the individual on the computer display and requires the user to use a computer keyboard to enter responses. The obvious problem with such an approach is that to the computer-illiterate individual, or to those individual user who are only marginally computer-literate, the computer keyboard is a formidable obstacle to completion of an entire questionnaire. Such an obstacle significantly affects the integrity and reliability of the collected data. (See, e.g., Maitland et al., *Archives of Physical Medicine and Rehab.*, Vol. 75, pp. 639–642, 1994.)

Yet other methods use a computer mouse system that an individual user must use to enter responses to the questionnaire. Such a system is next to impossible to use for someone who has not had extensive training or at least exposure to such computer technology. Using a mouse requires some dexterity and eye-to-hand coordination that may be difficult for some users.

All of the existing systems have significant drawbacks that, in one way or another, impact the ability of the system to procure valuable, reliable data from an individual user. Thus, there remains a need for a system that brings client questionnaires on-line to a computer, while maintaining the integrity of the collected data, that requires as little supervision as possible, and that provides an interactive and user-friendly interface as possible.

As a corollary to enhanced data collection capabilities, there is an increasing demand for enhanced data analysis, preferably in real-time. While systems and agencies presently exist which are capable of collecting patient data, such systems and agencies rely on manual collection techniques and semi-manual data analyses. For example, the American Academy of Orthopedic Surgeons (Rosemont, Ill.), recently issued a standard questionnaire to be used by practitioners to collect patient data. The data was manually collected, and then the collected data was sent back to the AAOS, in hand-written form, where the data was entered into a database. From the database, certain statistics regarding each particular patient was generated. Clearly, the data collection and analysis were not performed contemporaneously in that instance. However, the methodology used by the AAOS to collect and analyze patient data exemplifies the present state of the art.

Traditional statistical analysis techniques applied to patient data analyzes the data collected for an individual patient against historical data for that patient. The ability to compare data for an individual against a group would provide useful information for hospitals, insurance companies, and individual health care providers. For example, the progress of an individual patient over the course of a particular treatment, the responsiveness of a particular patient to a therapy, or the recovery rate of a particular patient, all as tracked against group norms, is useful for physical therapists, physicians, and insurance agents. If such analyses can be performed relatively contemporaneously with therapy or treatment, adjustments may be made during the course of the therapy or treatment to optimize effectiveness. Using currently available systems, there is a significant delay between data entry and obtaining the results of such analysis, if such analysis is even made available to a user.

Data collection methodologies currently in practice among hospitals, clinics, and the like, include either walking a patient through a series of questions as the system user enters the patient responses, or having the patient manually complete a paper copy questionnaire. In both instances, patient data is entered by a party other than the patient. Such systems potentially introduce transcription or other third party errors, making the data inherently suspect.

The same issues discussed above in connection with healthcare organizations exist in a variety of other organizations, such as automobile, transportation, and any service organizations. In such organizations, it may be desirable to identify group trends and individual activity compared against such group trends.

Accordingly, there remains a need for a computer system that allows a patient or user to directly enter data into the database for real-time analyses based on group, and not only on individual, dynamics. There further remains a need for a computer system that provides access to sufficient group data to enable essentially real-time correlations and statistics to be performed using demographic information to generate outcomes profile reports that may be used to analyze, inter alia, individual/patient satisfaction with particular treatments, in a health-care environment.

SUMMARY OF THE INVENTION

The present invention comprises a system for data input and storage and for correlation of such data against group data contained in a linked database. The data is input via a series of hierarchical menus, which menus may include sub-menus and fields that enable a user to directly input data for storage into the database.

In practicing the present invention in a medical records environment, the data preferably includes demographic data about each patient. The demographic data is used to generate an outcomes profile report in which individual data, e.g., data for an individual patient, are compared against historical data for individual data as well as against a user-specified group. Such demographic data also may be used in other application environments, such as sales, marketing, and manufacturing in which information relating to specific customers and vendors is maintained in a limited or relational database.

Another aspect of the present invention, in a healthcare environment, is the ability to collect patient data directly from a patient using questionnaires presented to a patient as a series of hierarchical user-driven display screens. The system provides an interactive, patient-friendly interface via a touch screen hardware interface through which the patient responds to questions. The patient's answers to subjective questions then are transformed into quantitative values that may be analyzed to determine trends and statistical significance regarding functional status, symptom severity, and patient satisfaction.

In practicing the present invention, a user inputs data concerning an individual, or the individual directly inputs such data. Once all data is input, an outcomes profile report is generated that reports certain quantitative comparisons and statistical analyses between the data for the individual and group data. A user may select certain sort criteria sets and subsets for selecting a specific group against which the individual data is compared and reported.

The invention is more completely described in the claims and in the specification, including the figures.

BRIEF DESCRIPTION OF THE FIGURES

FIGS. 8A–8B are graphic reproductions of sample Outcomes Profile Reports embodying the present invention.

FIG. 10B is a graphical representation of a Primary Physician menu of the embodiment of the invention shown in FIG. 10A.

FIGS. 18A–18H are graphical representations of patient questionnaire menus of an embodiment of the Questionnaire function of the embodiment of the invention shown in FIG. 13.

DETAILED DESCRIPTION OF PREFERRED EMBODIMENTS

The present invention relates to a system that permits a user to generate essentially contemporaneous individual-to-group statistical analyses based on information regarding individual data entered into a database. The present system enables an individual to enter individual data directly into the database, by a menu-driven user interface, without the use of third-party to input the data.

Figure 1:
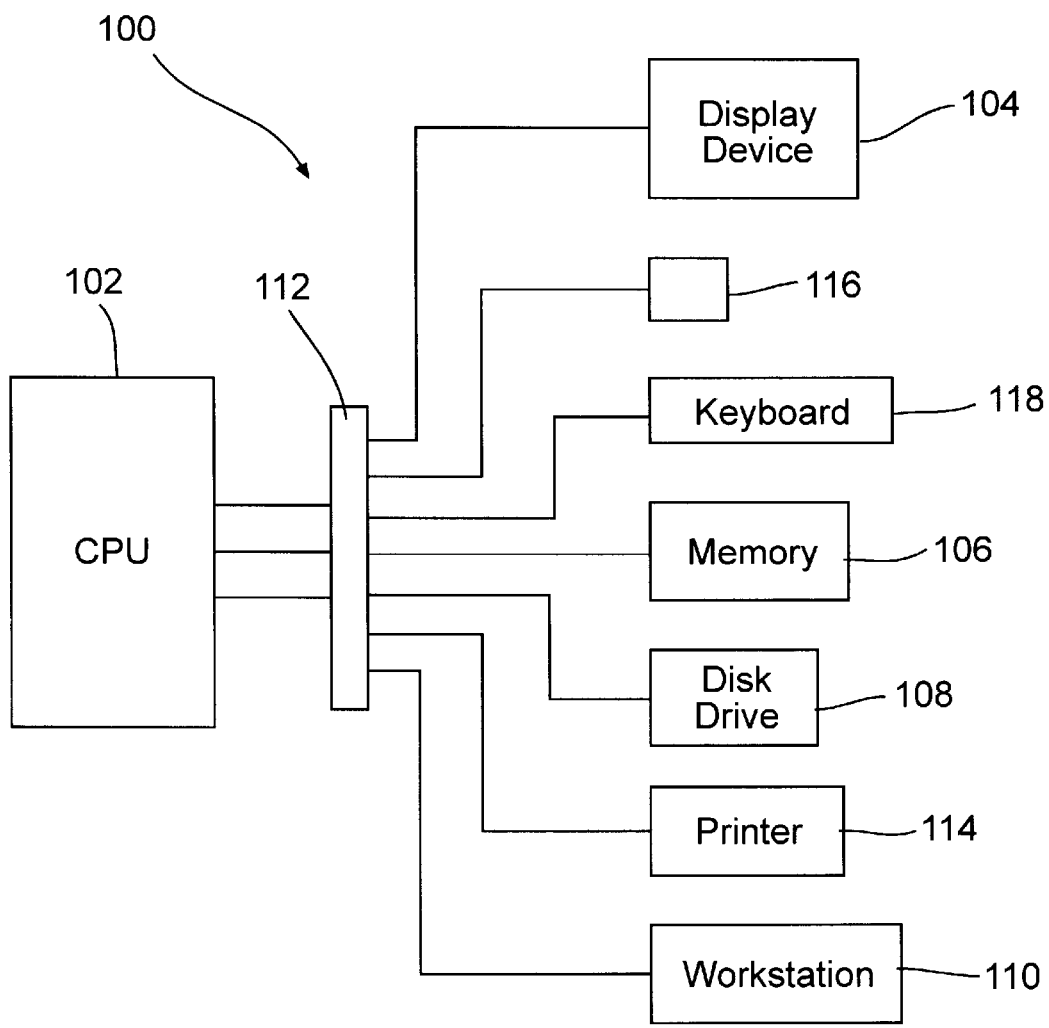
FIG. 1 is a block diagram showing a computer hardware environment of the system of the present invention.

In a preferred embodiment for practicing the present system, and as shown in FIG. 1, the present system may operate in a standard computer hardware environment 100, preferably comprising a central processing unit ("CPU") 102 in communication with a standard bus 112. The bus 112 is in communication with peripheral devices, such as a display device 104, a keyboard 118, a "mouse" or other user-driven input device 116, and a printer device 114, such as a laser jet or color printer. The bus 112 also is in communication with an addressable memory 106 and one or more disk or CD-ROM drives 108 or other memory devices on which a database may be stored. In alternative embodiments, the bus 112 may be in communication with other buses, and the communication between the various peripherals and memory may be distributed among one or more of the buses.

The CPU 102 preferably is controlled by the display device 104 in response to inputs supplied to the CPU by the display device 104 which, in a preferred embodiment, functions as an input device. Specifically, and in a most preferred embodiment, the hardware configuration consists of a touch-screen display device 104, such as one utilizing capacitive technology and touch screen presently commercially available from Microtouch Systems, Inc. (Methuen, Mass.) and a high resolution monitor of the type presently commercially available from Goldstar (Korea) and Mitsubishi Electric Corporation (Japan).

The CPU 102 may be programmed to operate in any operating system compatible with the hardware, such as DOS. The computer program that implements the present invention may be programmed using C or any other comparable application software presently available. In a very preferred embodiment, the CPU 102 is an IBM '486 personal computer, with 80 MHz, 510 Mbyte, upgraded to an 8 Mbyte RAM.

Alternatively, the display device 104 may be a conventional type display device as known in the art. For example, the display device 104 may be a raster-type display used with the CPU 102 in a conventional manner to produce images of characters generated from codes, such as ASCII. In that embodiment, the input device may be a conventional type, such as a keyboard 118 with a "mouse" type controller 116. In another embodiment, the data may be input by a combination of touch-screen input and keyboard/mouse input. In preferred embodiments, data from external devices 110, such as a Dexter™ Tradestation (available from Cedaron Medical, Inc., Davis, Calif.) may be ported directly from the external device to the bus 112 using standard porting techniques and hardware.

The database used in conjunction with the present system, primarily includes preselected data, menu functions, report definitions, menu definitions, and interactive display control. The database of report definitions and menu definitions are rules used to specify the number of menus and fields and their positions, the form of reports, and the like. These rules are used to retrieve input from the display device 104 and the work station 110 and store such input in the database in the form in which the user inputs unique data for each field.

The addressable memory 106 is a conventional type and preferably includes Random Access Memory (RAM) and Read Only Memory (ROM). The CPU 102 accesses information from the memory 106 in accordance with the operating sequences of the present invention. These operating sequences are directed to the display of a series of menus and fields, storing of the data input in response to such menus and fields, generating reports based on the data, and displaying and printing reports, as described in further detail below.

In a preferred embodiment, and as shown in FIG. 1, the CPU 102 is coupled to and receives data from a work station 110, such as the Dexter™ Tradestation. The work station 110 may be used to monitor and directly input patient data into a database via the CPU 102.

In practicing the present invention, the CPU 102 generates a first display on the monitor 104, prompting user input. The following discussion assumes that selections and options are exercised by the user by interacting directly with the monitor 104. In alternative embodiments, a user may make selections via an input device, such as a keyboard, a mouse, an electronic pen, or any other device as available.

The present system may be used in conjunction with a variety of databases. In the illustrated embodiment described below in detail, the system is used in conjunction with a medical records database. The illustrated medical records database is divided into five categories: demographics; present illness; past medical history; social; and text paragraphs. The disclosed system may be adapted for use with other or additional categories, or with other databases, such as marketing, sales, manufacturing, or other databases used for retrieving and storing data and from which reports based on historical and group data are generated.

Figure 2:
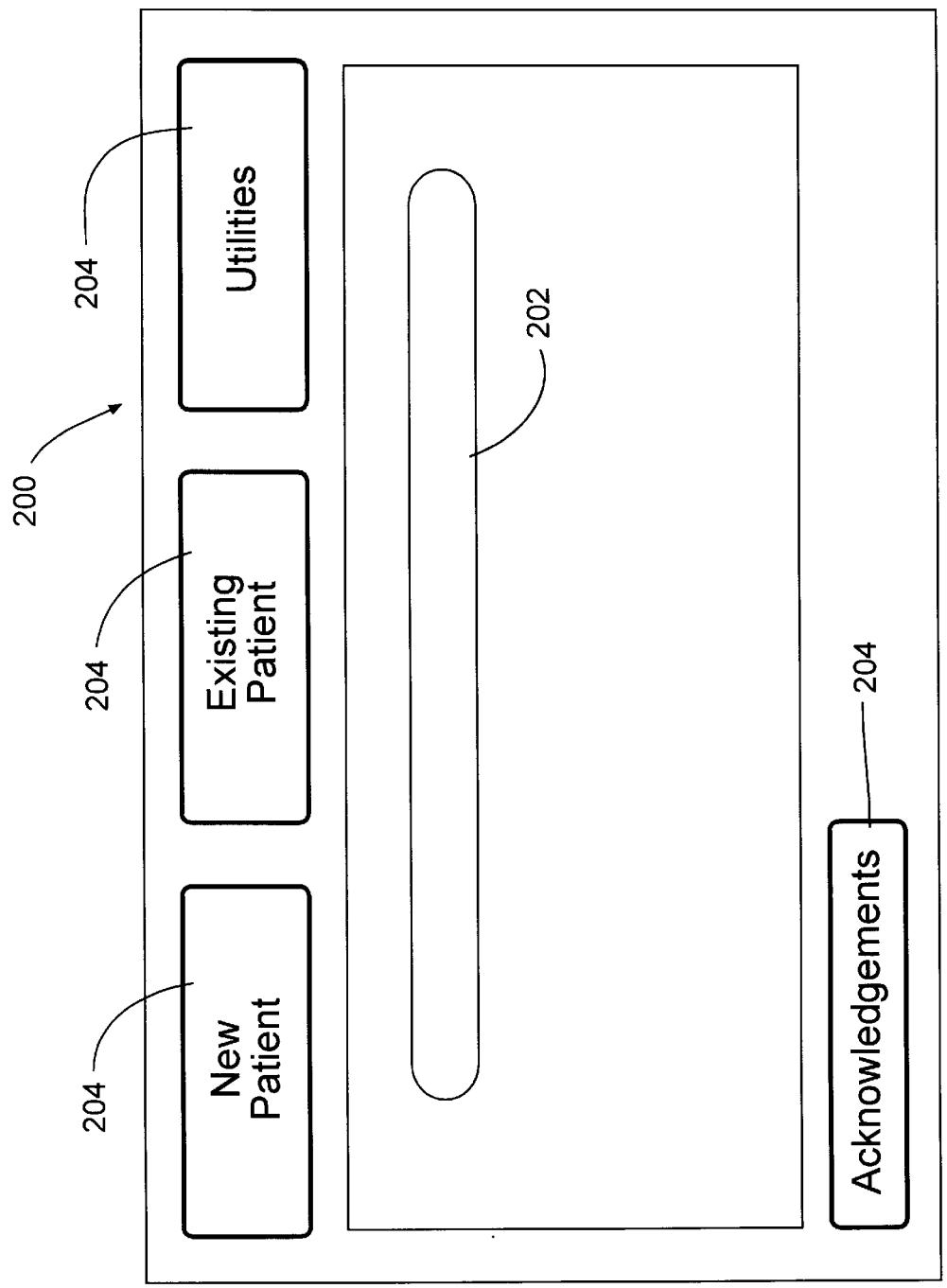
FIG. 2 is a graphical reproduction of a sample display menu embodying the present invention.

In one embodiment of the present system, a user is presented with a menu, such as the menu 200 illustrated in FIG. 2. A preferred menu 200 includes one or more fields 202 which the user completes or to which the user responds by inputting data or other information. The menu 200 further may include one or more buttons 204 which a user may activate by touching the image of the button 204 on the screen or by using any other available input device, to be presented with another menu 200. The menus 200 are hierarchically stacked in accordance with rules contained in the database. Thus, a user interacting with the present system may use buttons 204 presented in a cascade of menus 200 to input data in fields 202, which data is stored in the accessible memory 106 or added to the database for subsequent processing by the CPU 102.

Once data is entered and stored in the system 100, a user may sort and group patients contained in the database and perform an analysis on the group of patients in accordance with certain parameters selected by the user.

Figure 3A:
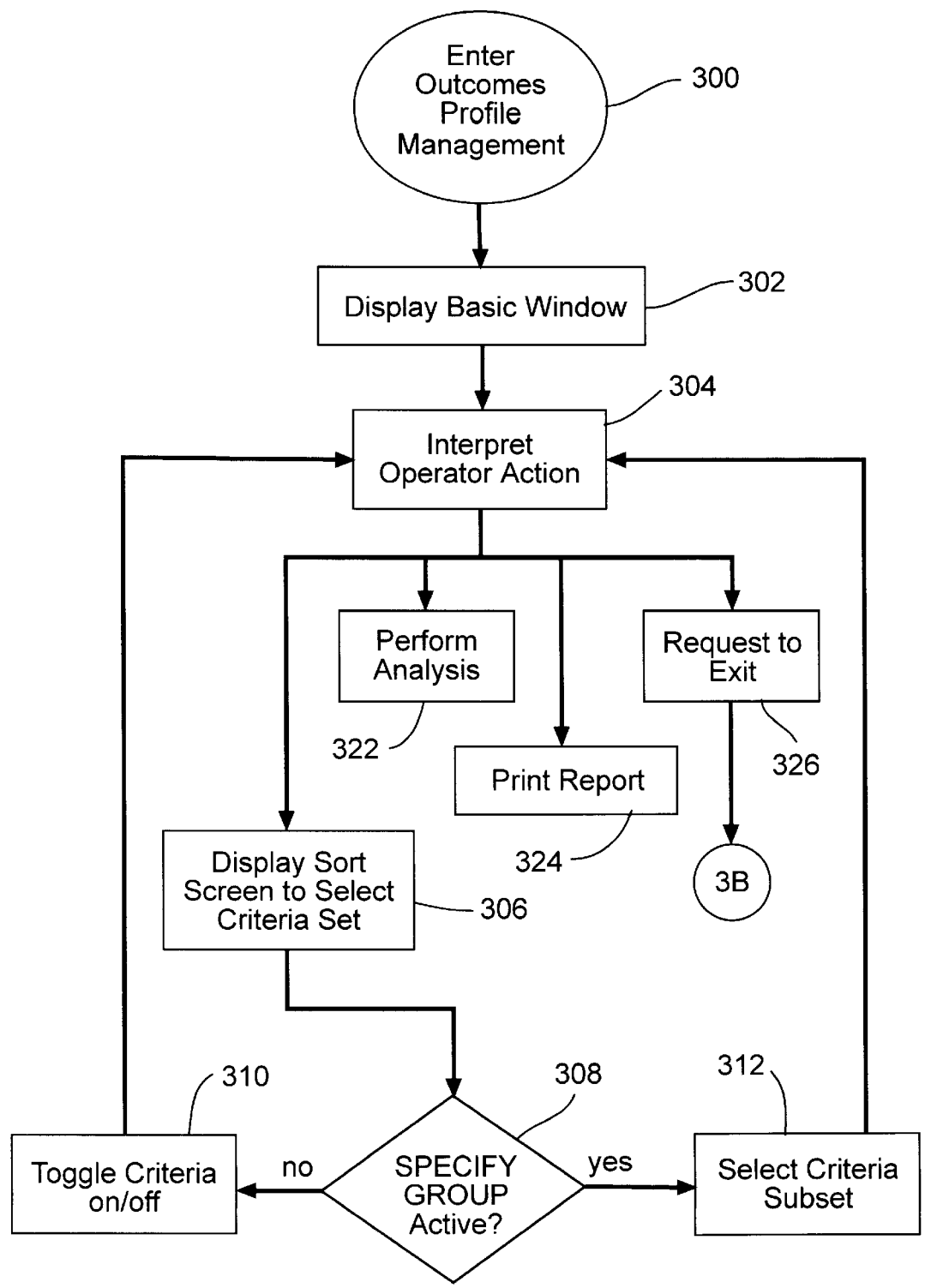
FIG. 3A is a flow chart overview of the outcomes profile management system of the present invention.

FIG. 3A illustrates a flow chart for a system for generating an outcomes profile report in accordance with the present invention. At the outset, the system enters the outcomes profile management program 300 at the request of a user responding via a Main Menu, such as that shown in FIG. 4.

Figure 4:
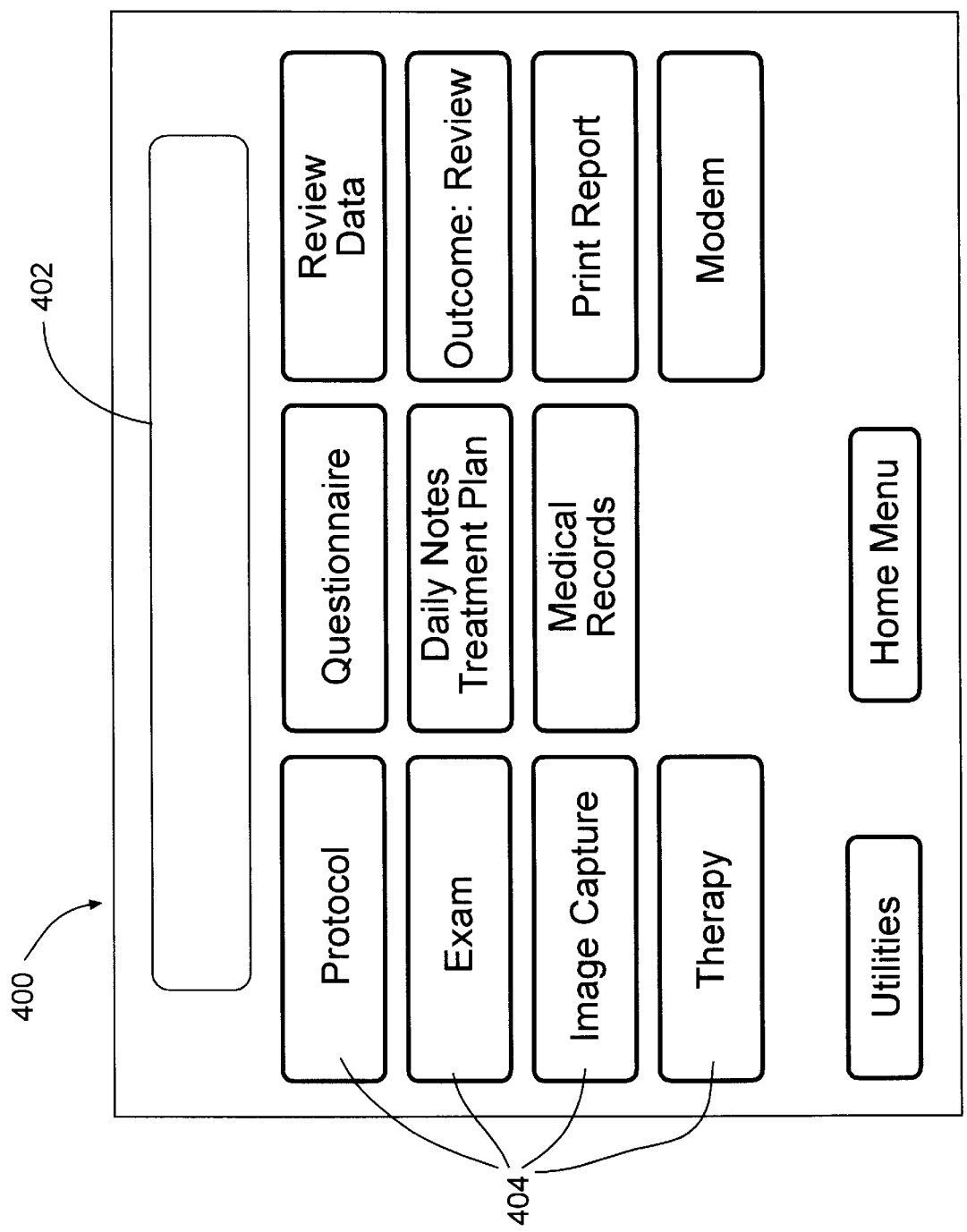
FIG. 4 is a graphical reproduction of a sample home menu screen of an embodiment of the present invention.

In the illustrated Main Menu 400 of FIG. 4, the Main Menu 400 includes a header field 402 that identifies the patient by name, and may include additional information, such as the time and date of the currently selected data file. The Main Menu 400 also includes several buttons 404 each of which may be selected by a user to access various functions of the system as identified on each button 404. The outcomes profile report of the present invention may be accessed via a button labelled "Outcome Review", "Outcomes Profile Report", or the like. In the illustrated embodiment of FIG. 4, the button is labelled "Outcomes Review". Alternatively, other pathways may be designed into the inventive system to enter 300 the outcomes profile management portion of the system.

The CPU 102 interprets the operator's action 304 in response to the displayed Main Menu 400. If the user selects "Outcomes Review" from the Main Menu 400, then a Basic Window is displayed 306 to enable the user to select sort criteria for defining the group to be used in the outcomes profile report. An example of a Basic Window of the type that may be generated by the system is shown in FIG. 5.

Figure 5:
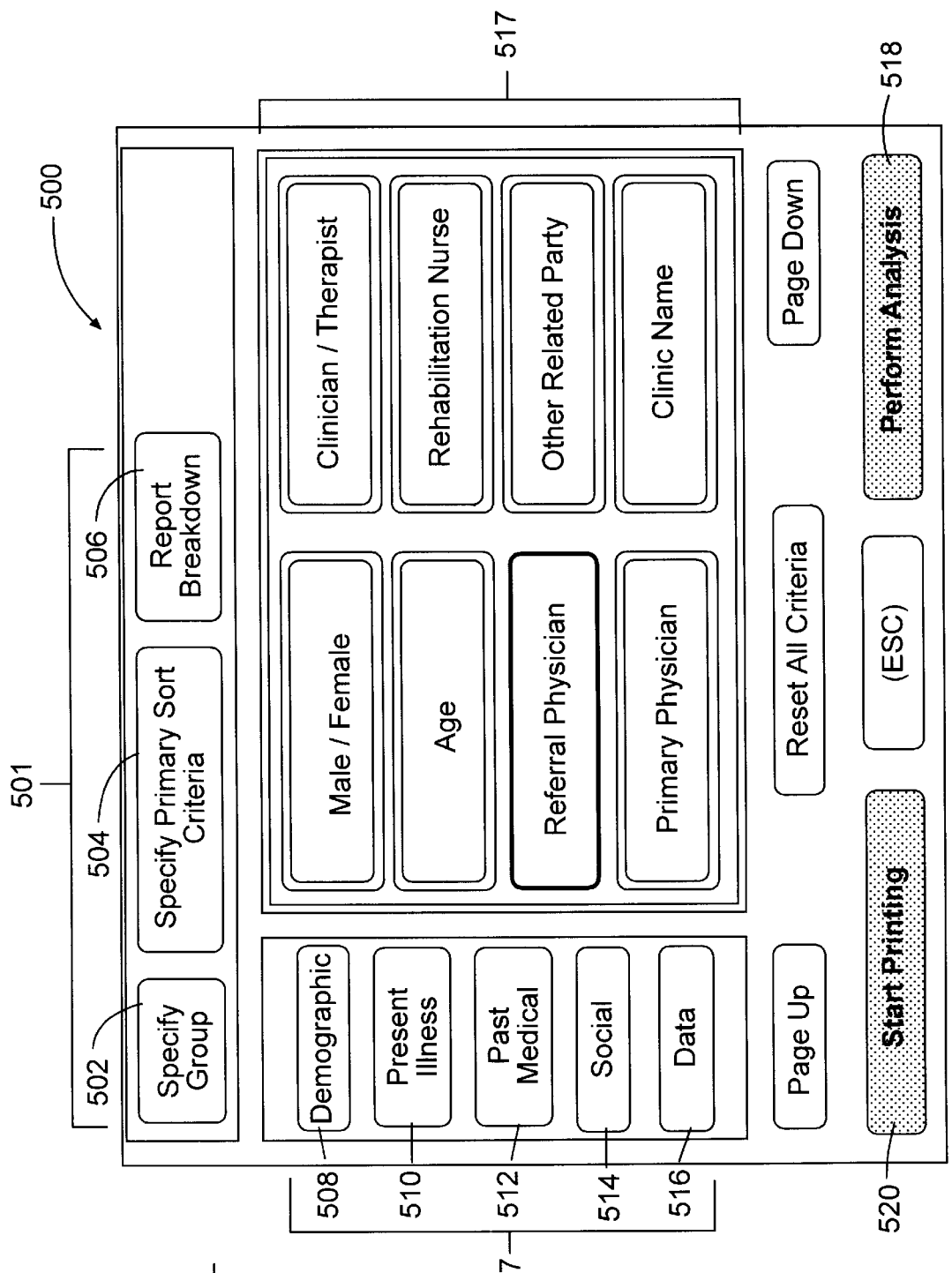
FIG. 5 is a graphical reproduction of a sample sort screen of an embodiment of the present invention.

The Basic Window 500 illustrated in FIG. 5 includes three primary buttons across the top, horizontal axis, for accessing the analysis functions for an outcomes profile report in accordance with the present invention. Their buttons are labelled "Specify Group" 502, "Specify Primary Sort Criteria" 504, and "Report Breakdown" 506 and may be used to access the corresponding menus. The analysis functions are applied to the records in the database based on selected sort criteria sets 507, identified in a set of buttons along the left vertical axis: Demographic 508; Present Illness 510; Past Medical 512; Social 514; and Data 516. Each sort criteria set 507 includes a subset 517 of sort criteria. In the illustrated example of FIG. 5, the Demographic sort criteria set 508 was selected, and within that set a user is presented with sort criteria subsets 517 labelled Male/Female, Age, Referral Physician, Primary Physical, Rehabilitation Nurse, Other Related Party, and Clinic Name. In the illustrated example, activating the "Referral Physician" button presents the user with a list of physicians from the database from which the user may select for the outcomes profile report. Returning now to FIG. 3, the system queries 308 whether the analysis function Specify Group 502 is active, i.e., selected by the user. If not active, the system toggles the criteria set on/off 310, and then returns to the Interpret Operator Action function 304. In the illustrated embodiment, a user must first select a Specify Group 502 analysis function, because this forms the high level function for generating an outcomes profile report of the present invention. If Specify Group 502 is active, the system enters the user selected sort criteria subset 312 from the display group 517, and then returns to the Interpret Operator Action function 304.

Once the sort criteria are selected by the user, the criteria are stored in the memory 106 until the user exits the Outcomes Profile Management window. While in the Outcomes Profile Management window after a sort is performed, the same criteria remains selected which allows a minor revision of those criteria and another sort to immediately be performed. Typically, the next operator action upon which the system interprets and performs typically is a request to perform a statistical analysis 322 in accordance with the present invention.

Alternatively, the system may, in response to an operator action, begin the process for printing an outcomes profile report 324 on the printer device 114. Alternatively, the system may execute a Request to Exit 326 the outcomes profile management portion of the system. This Request to Exit 326 leads to the window from which the outcomes profile management portion of the system was selected by the user. As discussed in further detail below, in a preferred embodiment, a user may access the outcomes profile management function through one of several modes. For example, in one mode a user may reach this window via a database function accessible via a Database button, while in another mode a user may reach this function directly via the Basic Window 400.

Figure 3B:
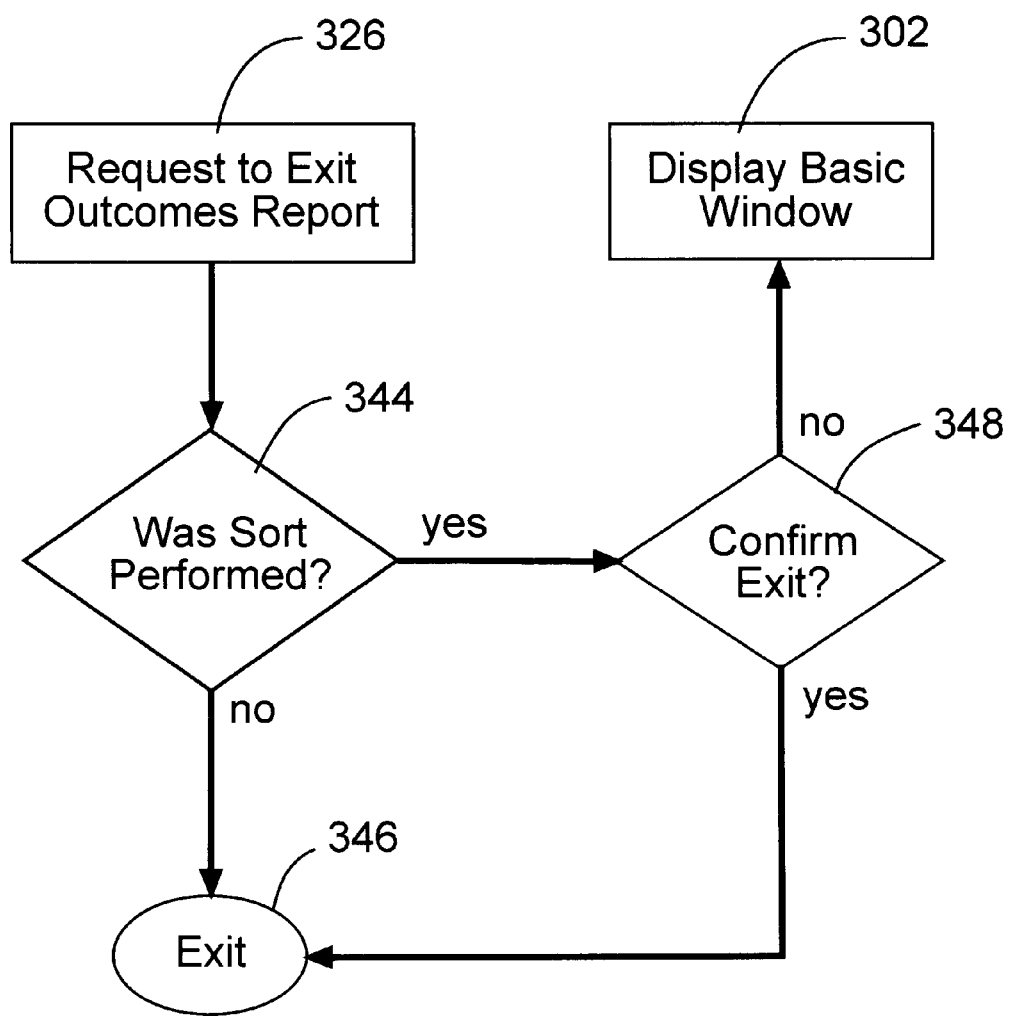
FIG. 3B is a flow chart of the request to exit function of the outcomes profile management system of the present invention.

In a preferred embodiment, and as shown in FIG. 3B, once a user requests to exit the Outcomes Profile Report function 326, the system queries 344 whether a sort was performed. If a sort was performed, the system may confirm 348, possibly by generating a display to such effect, whether the user wants to exit. If the user does not want to exit, then the Home Menu is displayed 350. If a sort was performed, or once the user confirms the request to exit the Outcomes Profile Report, then the system allows the user to exit the Outcomes Profile Report program 346.

Figure 6A:
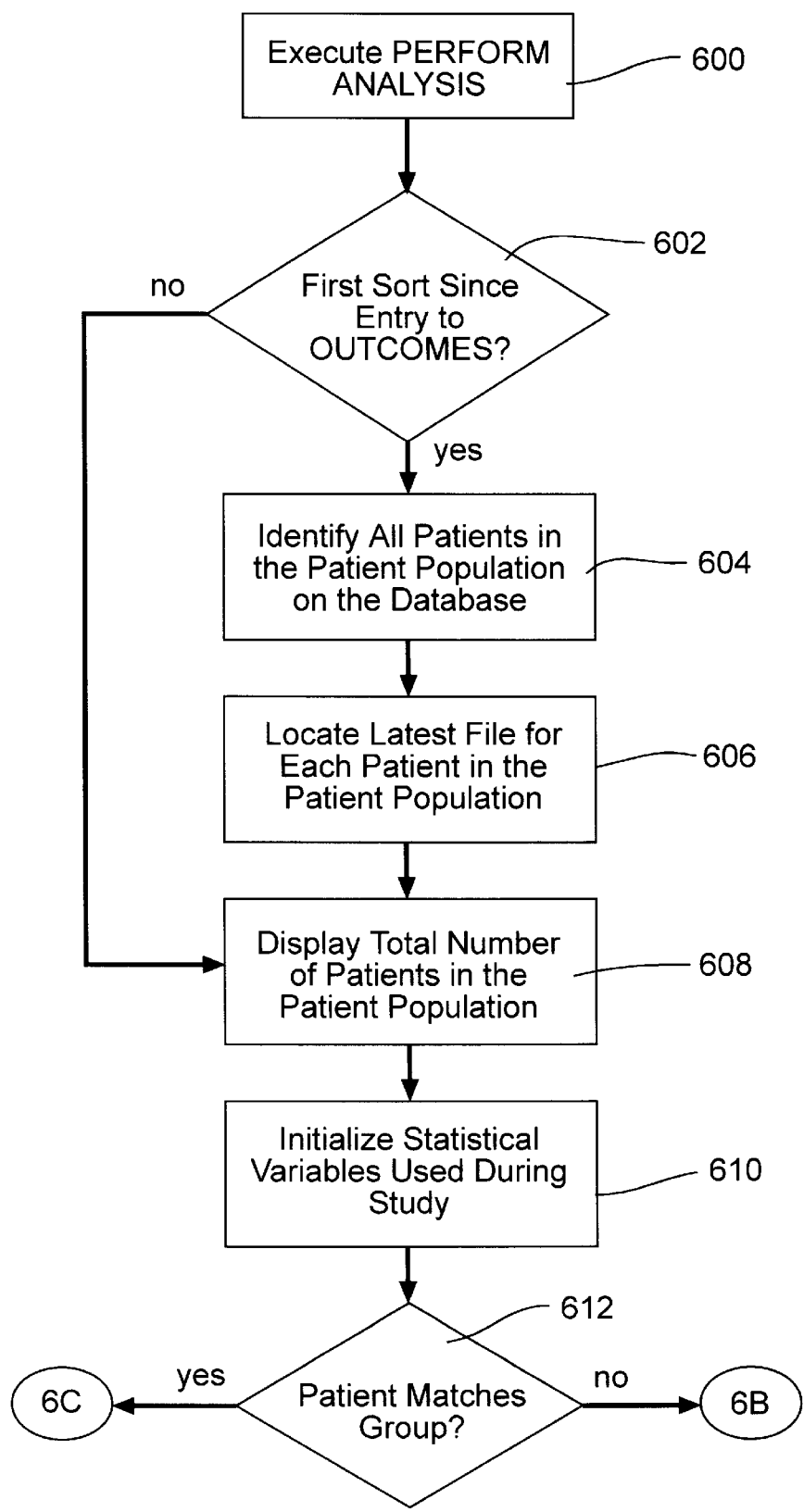
FIGS. 6A–6C, taken together, form a flow chart of a Perform Analysis function of an embodiment of the present invention.
Figure 6B:
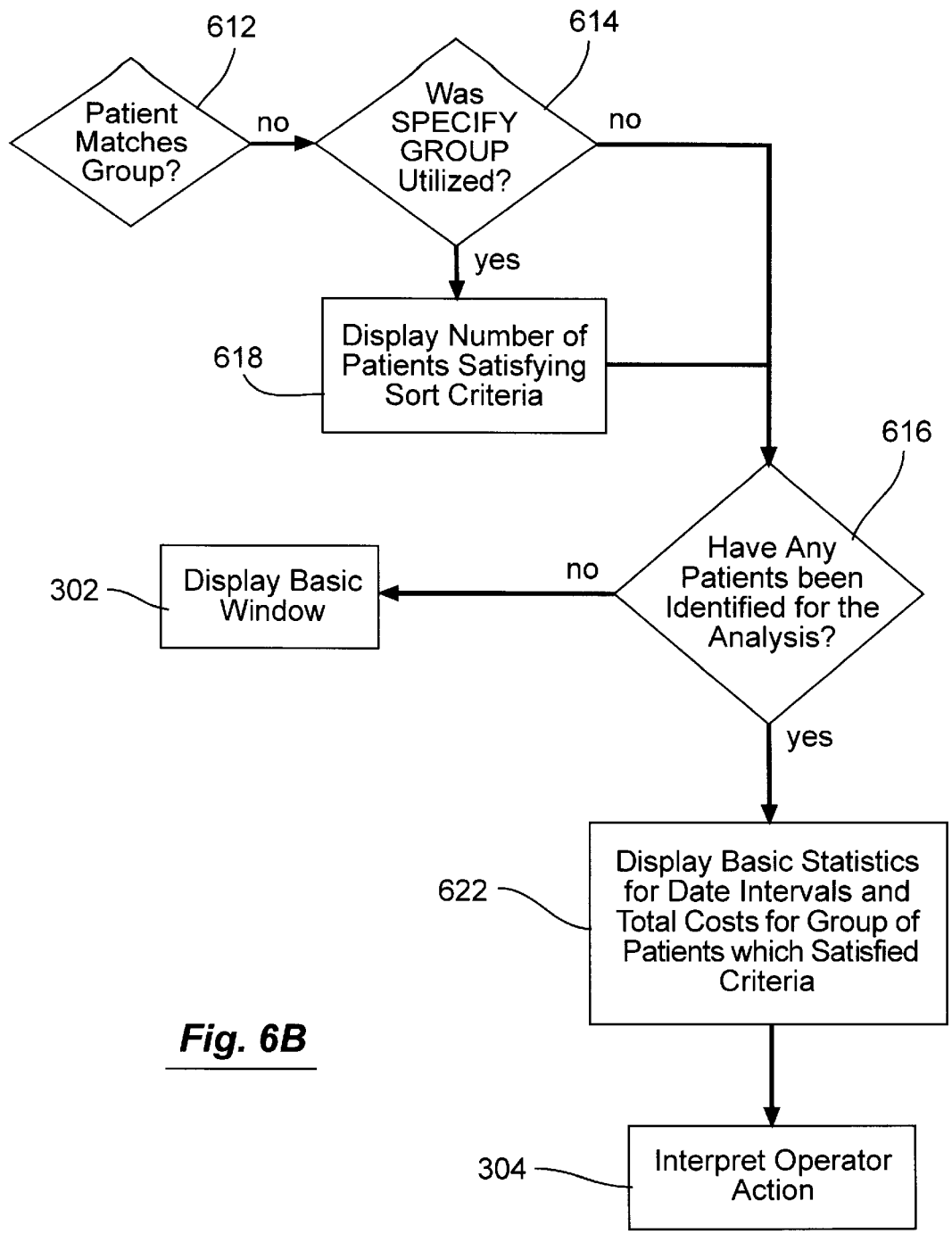
Figure 6C:
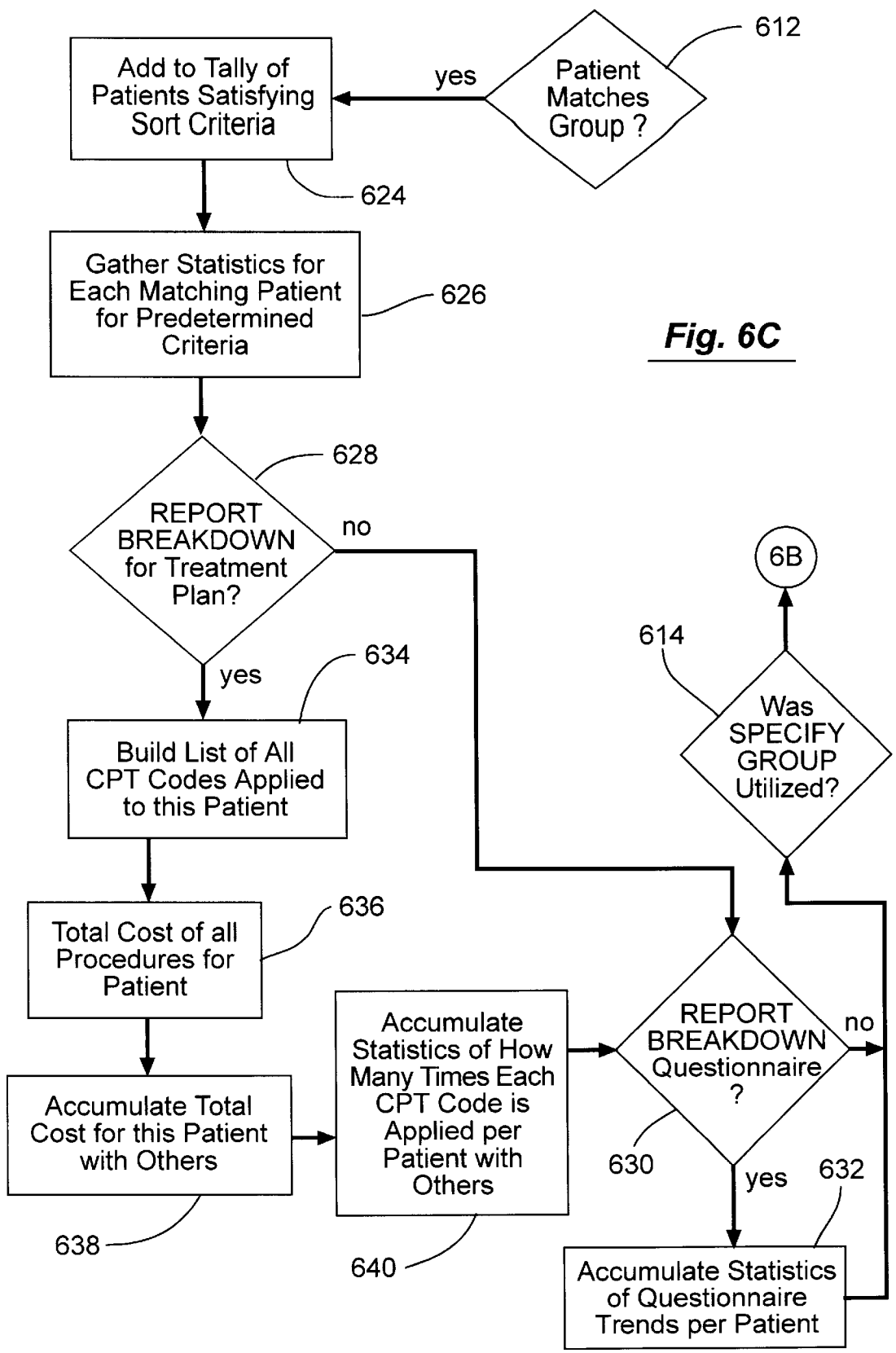

If a user activates a Perform Analysis button 518 on the Basic Window 500, the system begins performing the analysis 322 in accordance with the present invention, and as illustrated in FIGS. 6A–6C. As shown in FIG. 6A, the system begins executing Perform Analysis 600 with a query 602 whether the present sort is the first sort since the Enter Outcomes Profile Management 300 function. If not, then the total number of patients available in the patient population stored in the database are displayed 608 on the display device 104. If the query 602 is true, then all patients in the patient population stored in the database are identified 604 and the latest file for each patient in the patient population is located 606 in the database prior to displaying 608 the total number of patients in the patient population. That is, the most recent file for each patient in the database identified in step 606 is examined. Statistical variables used during the analysis are initialized 610, and the system queries 612 whether the individual patient upon which the report is being generated, matches the group data, i.e., the data for the patient population.

Turning now to FIG. 6B, if the query 612 is false, the system then queries 614 whether Specify Group was utilized. If not, then the system queries 616 whether any patients from the group have been identified for the analysis. That is, it is possible that there are no patients yet on the database, thus there is no group against which to perform an analysis. Even if a sort criteria was applied to a patient population, it may be possible that none of the patients in the patient population satisfied the sort criteria or, alternatively, survived the application of a sort criteria.

If Specify Group was used 614, then the number of patients in the database satisfying the Specify Group sort criteria is displayed 618 on the display device 104, and the query 616 is made after such display 618. If no patients satisfied the criteria, then the Basic Window is displayed 620 and the system cycles back through the Basic Window 500. Alternatively, if there are patients that satisfy the criteria, the basic statistics are displayed 622.

In a preferred embodiment, a set of rules for basic statistical analyses and report criteria are stored in the database and applied against data identified following performance of the sort function in accordance with user selected criteria, as described above. In the illustrated embodiment, such report criteria include: days from injury to first surgery; days from initial rehabilitation to discharge; days from injury to discharge; total number of visits. Additional or other predetermined analyses may be included in the system, depending on the specific application. The basic statistical analyses include averages and standard deviations, but additional tests and analyses may be performed, as required by a specific application. Without other sorting requests, the mean time between events of the present illness is calculated. Once the display is generated 622, the Basic Window 500 preferably is displayed 302 to enable a user to selectively print the outcomes profile report. In a preferred embodiment, the outcomes profile report is not saved in memory and should immediately be printed before exiting the outcomes profile management menu. In an alternative embodiment, it may be possible to save an outcomes profile management report generated under this function.

If the result of the "patient matches group" query 612 is that the subject patient does match the sorted group then, turning now to FIG. 6C, the subject patient is added to the tally of patients satisfying the sort criteria 624. Statistics for each patient matching certain predetermined sort criteria, such as date intervals and number of visits, is collected 626 and stored in memory 106. The system next queries 628 whether there is a user-selected Report Breakdown sort criteria subset 517 for the parameter "Treatment Plan." If the 628 query is false, then a follow-up query 630 regarding whether there is a user-selected Report Breakdown sort criteria subset 517 for the parameter "Questionnaire." The "Treatment Plan" and "Questionnaire" parameters is that the information for these parameters must be retrieved by examining all files for the identified patients, rather than being contained in the most recent file for a patient noted at 606. A much longer analysis time is required when either of these two parameters is activated due to the extra file searching.

If the query 630 is true, then statistics of questionnaire trends per patient are accumulated 632 and stored in the accessible memory 106. If the query 630 is false, then the system queries 614 whether Specify Group was utilized (see FIG. 6B).

If the query 628 regarding Report Breakdown for "Treatment Plan" is true, then the system builds a list of all Current Procedural Terminology ("CPT") codes (published and updated by the American Medical Association) applied to this patient 634. The cost of all procedures for the subject patient is totalled 636 and stored in the accessible memory 106, and a total cost for this patient together with the other patients satisfying the sort criteria is accumulated 638. This step determines the minimum and maximum total cost for any patient in the group selected for analysis, in addition to a total cost for later mean and standard deviation calculations.

In addition, various statistics regarding the patient in contrast with the other patients in the identified group, such as the number of times each CPT code is applied per patient versus the group are accumulated 640. The system then applies the earlier query 630 whether there is a Report Breakdown criteria selected for questionnaire. Thus, the number of times each treatment (as referenced by CPT code) was performed on a patient in the group is determined.

Figure 7A:
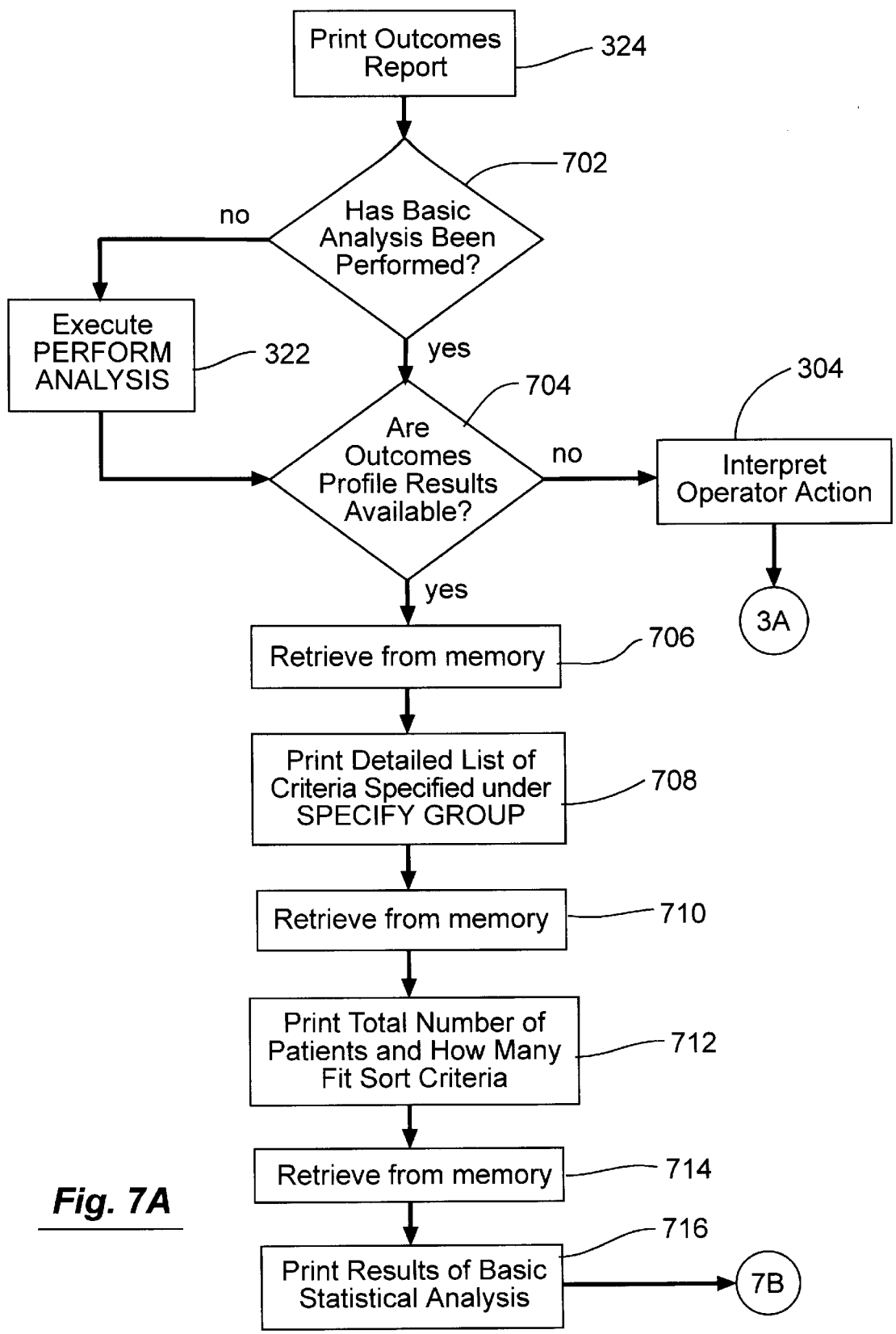
FIGS. 7A–7B, taken together, form a flow chart of a Print Outcomes Report function of an embodiment of the present invention.

From the Basic Window 500 a user may activate the Start Printing button 520 to print a copy of the generated outcomes profile report. Referring to FIG. 7A, the system responds to a Print Outcomes Report action request 324 from a user with a query 702 whether the basic statistical analysis was performed, i.e., performed on the Specify Group sort criteria. If no such analysis has been performed, the system returns to the Perform Analysis function 322.

Once the analysis is complete, or if the query 702 is true, the system next queries 704 whether outcomes profile results are available. If such results are not available, the system returns to Interpret Operator Action 304. If results are available, the system retrieves from memory 706 and sends 708 to the printer device 114 a detailed list of criteria specified under Specify Group.

The system next retrieves 710 from memory and prints 712 the total number of patients in the database and the number of such patients who fit the Specify Group sort criteria. The results of the basic statistical analysis performed as part of the outcomes profile report is retrieved from memory 714 and sent 716 to the printer device 114.

Figure 7B:
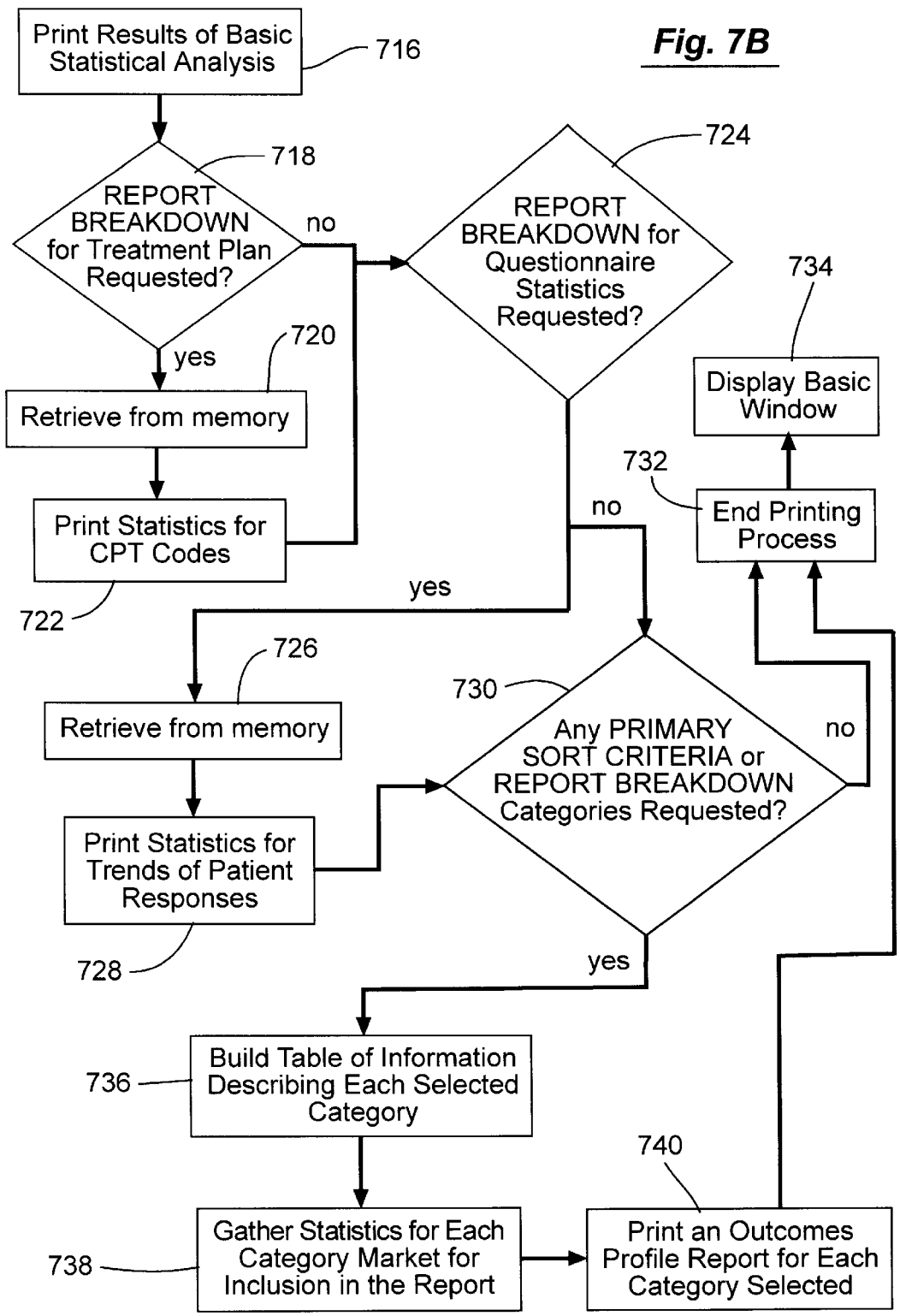

Continuing to FIG. 7B, the system queries 718 whether an analysis based on Report Breakdown for the "Treatment Plan" parameter was requested. If true, the statistics for the CPT codes are retrieved from memory 720 and sent 722 to the printer device 114. If no Report Breakdown for the "Treatment Plan" parameter was requested, the system queries 720 whether an analysis based on Report Breakdown for the "Questionnaire Statistics" parameter was requested. If true, the statistics for trends of patient responses, performed at step 632, are retrieved 726 from the memory and sent 728 to the printer device 114.

If no Report Breakdown for the "Questionnaire Statistics" parameter was requested, the system queries 730 whether any Primary Sort Criteria or Report Breakdown sort categories were requested. If none were requested, then the printing process ends 732 and the Home Menu is displayed 734. If such categories were requested, then the system builds a table 736 of information describing each selected category, and stores the table in the memory 106. Statistics are gathered 738 for each category marked for inclusion in the final printed report, as shown at 310 in FIG. 3. These categories will reflect the distribution of all possible results in each selected category for each patient satisfying the criteria subset using Specify Group, i.e., the patient population selected for analysis. The table of information together with the statistics are compiled and sent 740 to the printer device 114 to form the printed outcomes profile report.

An example of a basic outcomes report is found in FIG. 8A. In that illustrated example, the Specify Group sort criteria was "Referral Physician". Note that only the system-generated statistical analyses were performed, i.e., days from injury to first surgery, days from initial rehabilitation to discharge, days from injury to discharge, and number of visits. In alternative embodiments, the database may include rules for generating some base level statistical analyses as relevant to the particular specific application.

FIG. 8B shows a detailed outcomes profile report generated using Specify Group sort criteria of "Male Patients", Primary Sort Criteria of "Symptoms", and Report Breakdown of "Referral Physicians". Note that the generated table includes all three sort criteria. In alternative embodiments, it may be possible to generate a three-dimensional table based on four criteria or a table based on two criteria, depending on the capabilities of the hardware and the user requirements. In the illustrated embodiments of FIGS. 8A and 8B, the only statistical analysis performed is averages and standard deviation. However, in alternative embodiments, it may be possible to add other statistical analyses as appropriate.

The outcomes profile report generating system of the present invention relies upon the existence of data either residing in the database or input by a user, as described above. The user, for purposes of data input, may either be the same user as the individual requesting the statistical analysis, or may be the subject individual of the outcomes profile report. The preferred embodiment for entering data into the system for purposes of generating the outcomes profile report are described below.

After initializing the system, the user is presented with a Home Menu display 200 on the display device 104. An example of a preferred form of the Home Menu display 200 is shown in FIG. 2, described above. The Home Menu 200 preferably includes a set of display buttons 204 that permit a user to maneuver through the system 100. The buttons 204 may be activated by various input means, depending on the particular hardware and software configuration. For example, a user may activate a button 204 by touching the display screen directly, by directing and using a mouse or other tracking device, or by inputtin, information directly via a keyboard, vocal command, or other commercially available data input device.

Figure 9A:
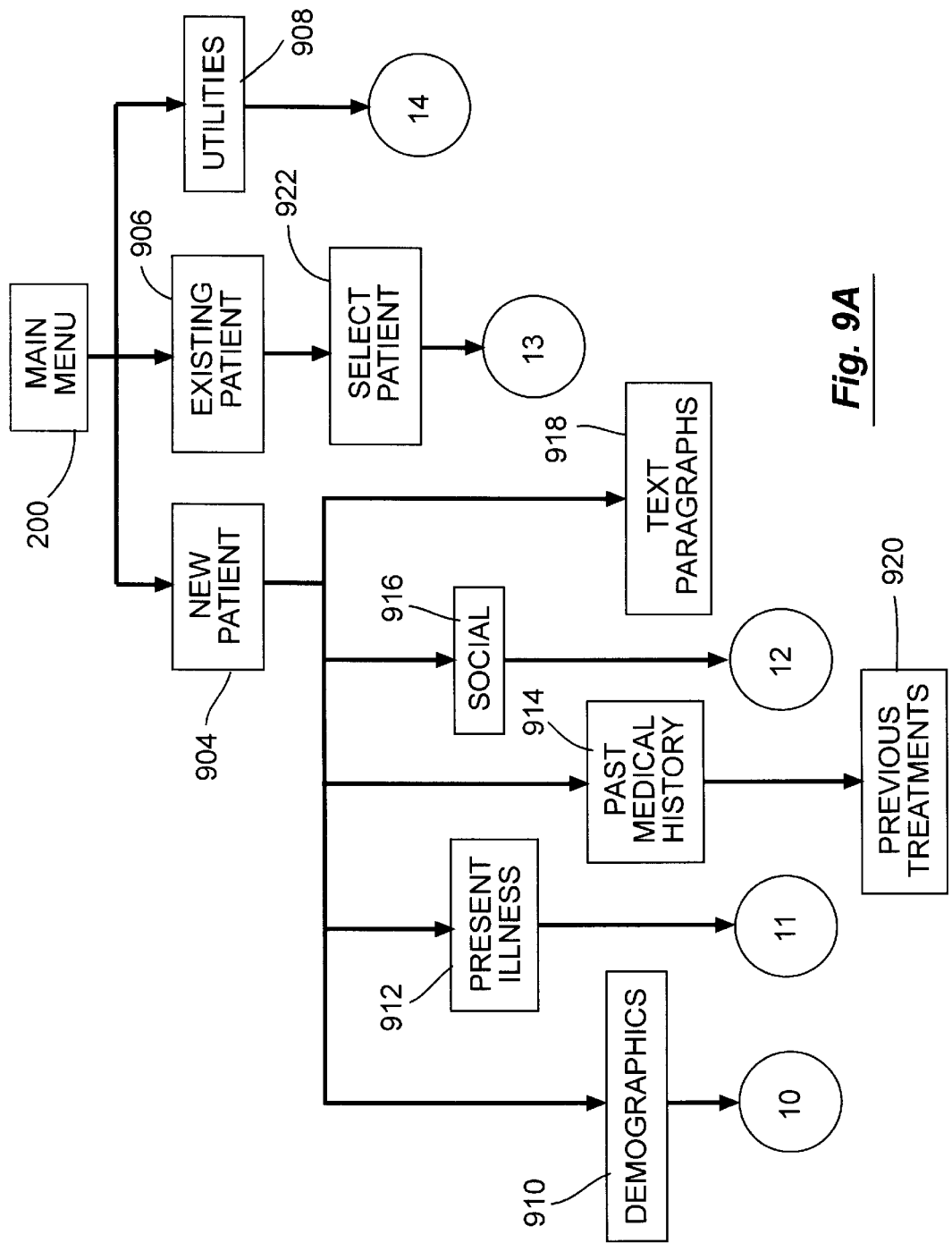
FIG. 9A is an overall hierarchical chart of the Main Menu of an embodiment of the present invention.

Turning now to FIG. 9A, the Home Menu 200 includes display buttons for entering data on a new patient via a New Patient menu 904 or on an existing patient via an Existing Patient menu 906, or for accessing utilities via a Utilities menu 908, each of which menu is described in further detail below. The New Patient menu 904 includes buttons which, upon activation by a user, lead the user to Demographics 910, Present Illness 912, Past Medical 914, Social 916, and Text Paragraphs 918 menus.

Some of these menus include buttons that lead to sub-menus or to alternate screens for entering data. For example, the Past Medical History menu 914 includes a button leading the user to a Previous Treatments menu 920. In the Existing Patient menu 906, a user may activate a button that leads the user to a Select Patient sub-menu 922, which in turn has additional sub-menus, as described in detail below.

Figure 9B:
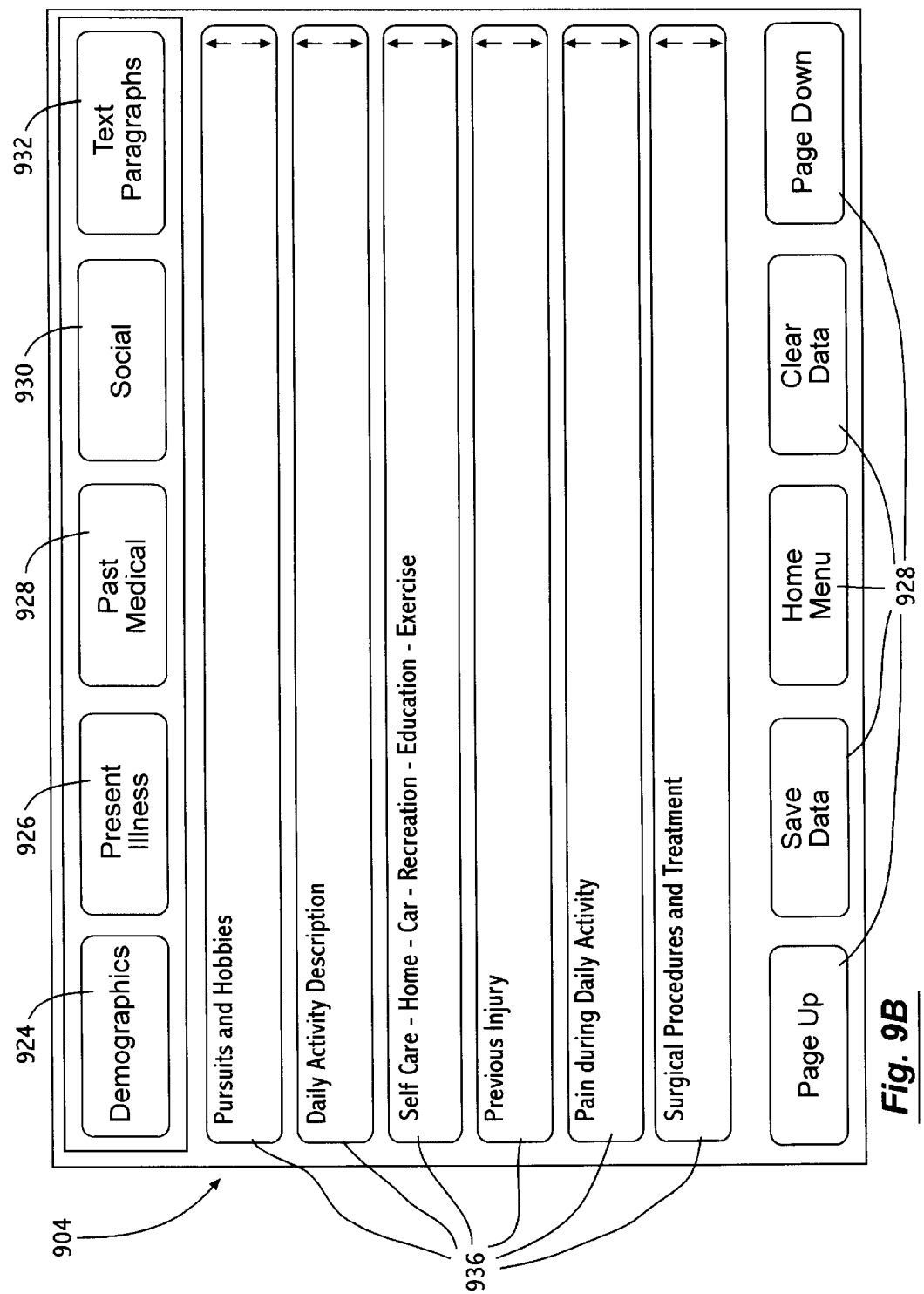
FIG. 9B is a graphical reproduction of a Main Menu of the embodiment of the invention shown in FIG. 9A.

An example of the New Patient menu 904 is shown in FIG. 9B. As illustrated, that menu 904 includes a "demographics" button 924, a "present illness" button 926, a "past medical" button 928, a "social" button 930, and a "text paragraphs" button 932, each of which may be activated by the user to display sub-menus for Demographics 910, Present Illness 912, Past Medical 914, Social 916, and Text Paragraphs 918, respectively. That menu 904 further includes various fields 936 for entering data, and additional function buttons 928 for performing basic functions such as scrolling up or down a page, saving data, clearing entered data from the menu, and moving back to the Home Menu 200.

Figure 10A:
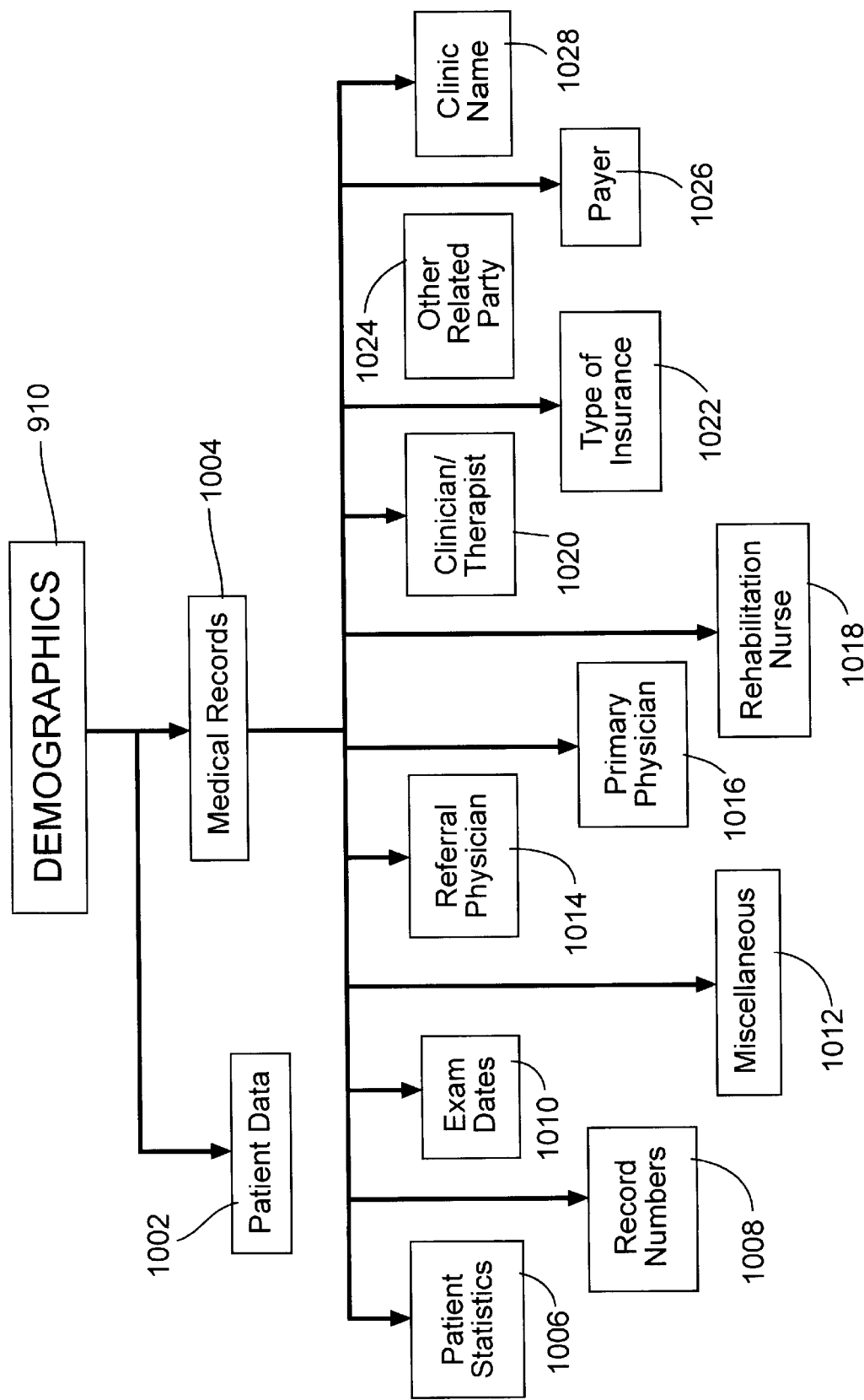
FIG. 10A is a hierarchical chart of the Demographics menu of an embodiment of the present invention.

In the illustrated embodiment of FIG. 10A, the first screen presented to a user after activating the button for the Demographics menu 910 is a Patient Data menu 1002, which preferably includes an initial screen having fields for entering basic patient data, such as patient name, street address, and telephone numbers. Additional information that may be useful about a patient, such a social security number, birthday, gender, and contact persons also may be included in this menu 910. Such information typically is entered about a new patient by a user. In alternative embodiments, for example for use of the present system in a sales environment, this initial screen may be used to enter data regarding customers.

The Demographics menu 910 may include multiple "pages" or multiple screens which are either presented serially to the user or through which the user may scroll. In the illustrated example, the user may scroll past the Patient Data menu 1002 to reach a second menu, such as a Medical Records menu 1004 as shown in FIG. 10A, which menu 1004 includes a menu with additional buttons and fields relating to demographics for each patient. Such menus having multiple "pages" typically include buttons for scrolling a page forward and/or a page backward from the displayed menu. In a preferred embodiment, each menu includes a button for returning to the Home Menu 200, a button for saving the entered data, a button for clearing the entered data, and an "escape" button. The "escape" button may either present to the user the Home Menu 200, the previously displayed menu, or an exit option from the system, depending upon where the user is positioned within the system at the time.

After a user enters the pertinent information in the Patient Data menu 1002 of the Demographics menu 910, a user is presented with a Medical Records menu 1004, for entering additional relevant patient data. As illustrated in FIG. 10A, the Medical Records menu 1004 may include several separate fields for entering: patient statistics 1006, such as the patient's full name and age, and various physical characteristics such as height and weight; medical record and/or patient identification numbers 1008; various examination dates 1010, such as the current date and any previous examination dates; and miscellaneous patient information 1012 such as language, ethnicity, and the dominant side (i.e., left- or right-side dominant) for purposes of relating to physical dexterity and flexibility test data that may be entered. Additional information may be entered into other fields, such as: the physician who referred the patient 1014 to the user; the primary physician treating the patient both in the past and currently 1016; the rehabilitation nurse 1018; and the clinician/physical therapist 1020, as appropriate. In addition, other fields may be made available for entering information regarding: the patient's type of insurance 1022, such as private insurance, federal (Medicare), state (Medicaid), worker's compensation, self-pay, automobile insurance, and the like; any other related party to the patient 1024, such as other forms of reimbursement available to the patient; the name of the individual or insurance company who will be paying the patient's expenses 1026; and the clinic name 1028 at which the examination of the patient was performed, which may automatically be entered at the time the system creates the data file. These fields may be presented to the user in a single menu format, or may be presented on multiple menus through which a user scrolls using, e.g., one or more scroll buttons.

In a preferred embodiment of the present invention, one or more of the fields in the Medical Records menu 1004 are automatically generated by the system. For example, in the illustrated example shown in FIG. 10A, one or more of the "Exam Dates" fields 1010 are entered. A current exam date may be entered automatically to reflect the date the record is being accessed by the user. Most fields in the menus and submenus of the New Patient menu 904 are entered by user because essentially no data exists for that patient. In other applications using the present system, such as in a sales or inventory tracking application, several fields may be automatically filled in by the system, using standard programming methods known and used by those skilled in the relevant art.

In a preferred embodiment, several of the fields are directly linked to a database containing predetermined field information. For example, in the "Primary Physician" field 1016, a user may activate the field, similar to activating a button, and be presented with a menu that includes fields for identifying a primary physician, such as the menu shown in FIG. 10B. In that illustrated embodiment, once the "Name" field is completed by the user, all other relevant fields are entered automatically from the same information contained in a database linked with the menu.

In a preferred embodiment, certain fields of a menu are linked to a database such that any changes made to these linked fields in the database will be reflected in the corresponding fields in the menu. Similarly, if the data contained in one of such fields is changed in the menu, then that data is changed in the database. For example, if the address of the primary physician has changed, and such change is entered in the Primary Physician menu 1016, that data is stored in the database, and the next menu that recalls the same physician will reflect the changed address.

In the illustrated menu 1016 of FIG. 10B, there is shown a "Select From List" button 1017. Activating that button 1017 results in the display of primary physicians listed in the database and linked or otherwise correlated with that menu 1016. In this manner, instead of entering a physician's name in the name field for that menu 1016, a user may retrieve a list of primary physician names from the database. Selecting any of the primary physicians from the retrieved list will not only import that primary physician's name from the database, but also will import the relevant data associated with that primary physician from the database.

In a preferred embodiment, several other lists are available for importing throughout the system. Essentially any of the other fields in the Medical Records menu 1004 may function as buttons that link to data in a linked database. This linking feature of the present system may be used in any other application, such as in an sales or manufacturing context in which the name and relevant data regarding certain referral agencies or certain parts suppliers is included on a central database to which the present system is linked by certain of its fields.

Figure 11A:
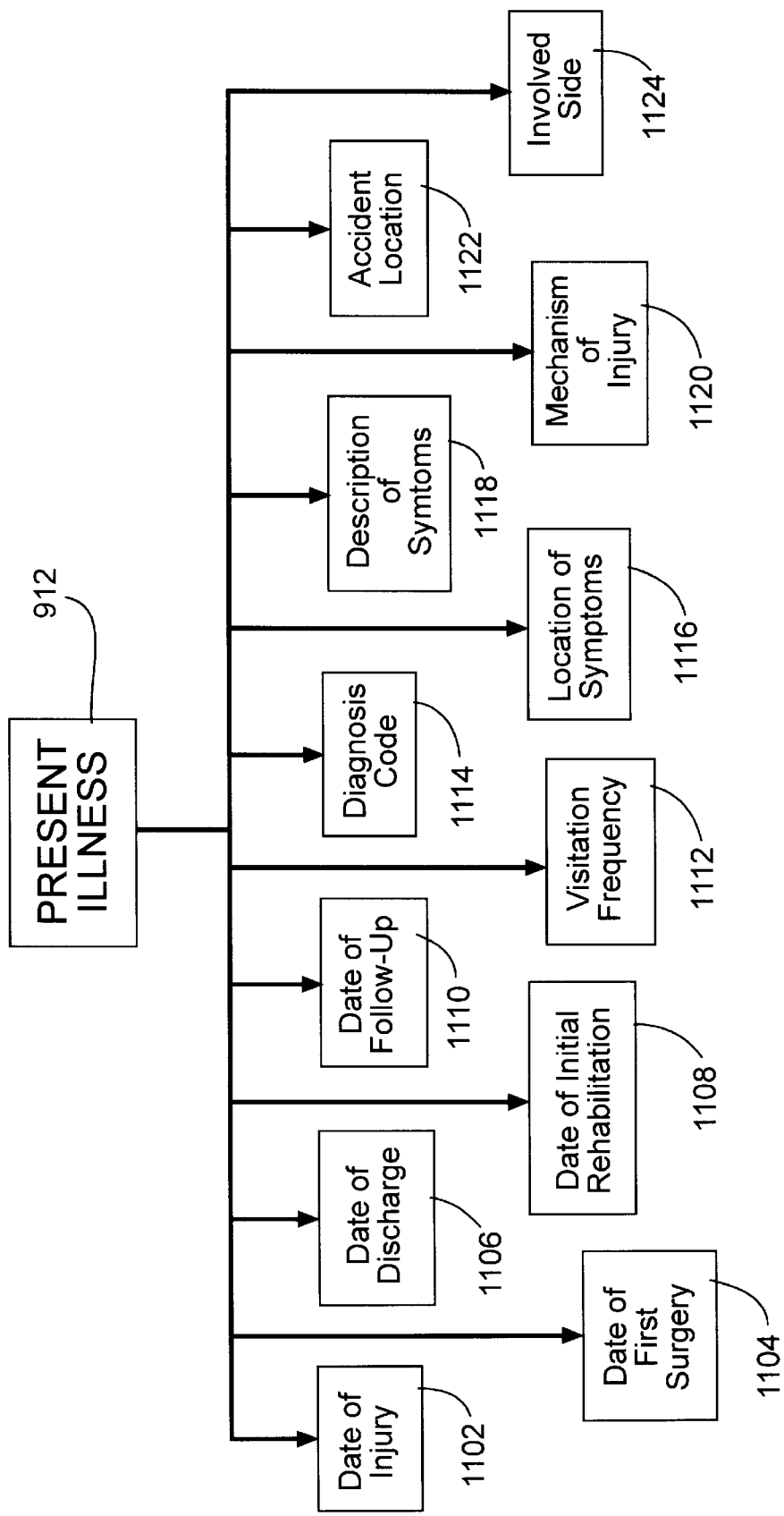
FIG. 11A is a hierarchical chart of the Present Illness menu of an embodiment of the present invention.

As illustrated in FIG. 11A, the Present Illness menu 912 presents a user with several fields for entering data relating to diagnosis and important dates of the pathology for a new patient. In the illustrated embodiment, these fields include: "Date of Injury" 1102; "Date of First Surgery" 1104; "Date of Discharge" 1106; "Date of Initial Rehabilitation" 1108; "Date of Follow-up" 1110; "Visitation Frequency" 1112; "Diagnosis Code" 1114, preferably corresponding to the International Diagnostic Codes (ICD-9 codes), published by the World Health Organization or, alternatively, the codes published by the U.S. Health Care Financing Agency, by main category grouping; "Location of Symptoms on the Patient" 1116; "Description of Symptoms" 1118; "Mechanism of Injury" 1120; "Accident Location" 1122; and "Involved Side" of patient's body 1124.

The data entered in the fields contained in the Present Illness menu 912 are important for generating an outcomes profile report and other reports as required by the user. The general display and performance of the fields contained in the Present Illness menu 912 are similar to the display and the performance of fields contained in the previously described Demographics menu 910. Specifically, the "Diagnosis Code" field 1114 may be activated to access a listing of standard diagnosis Codes by main category group. The user may then select one of the codes from the listing to be inserted into the "Diagnosis Code" field 1114. Preferably, upon selecting the "Diagnosis Code" field 1114, the user is presented with a full menu into which the user may enter the patients primary present illness. Upon entering that data, a list of specific codes then is displayed and the user may select one of the codes for automatic insertion into the "Diagnosis Code" field 1114. Also in a preferred embodiment, a search function is associated with the code listing to enable a user to search for any or all key words relating to the body part, pathology or procedure contained in the code description. Unlike most other fields, the "Diagnosis Code" field 1114 preferably permits a user to enter more than one input value for that field.

Figure 11B:
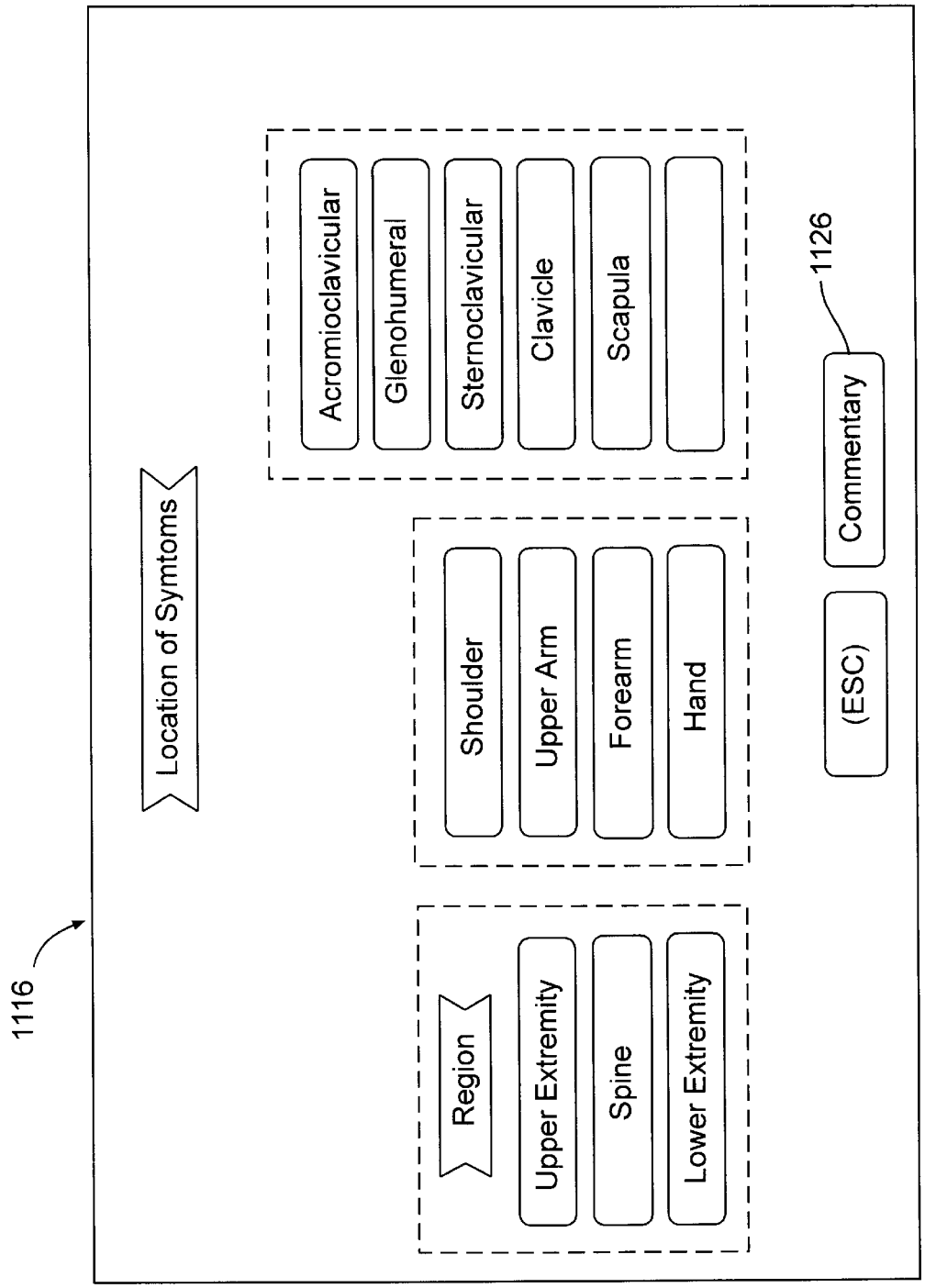
FIG. 11B is a graphical representation of a Location of Symptoms menu of the embodiment of the invention shown in FIG. 11A.

As an alternative or in addition to the ICD-9 coding of the diagnosis, a user may choose to use the generalized description of the present illness by selecting the "Location of Symptoms" field 1116. Such a generalized description of the location of the symptoms essentially is presented as a menu of body parts that increases in specifics as the user moves from across the menu, as illustrated in the sample screen of FIG. 11B. Clearly, in such a field the user should be able to select more than one option from the menu fields. In this particular menu 1116, a user may merely select a particular button and the data corresponding to that particular button is entered into the "Location of Symptoms" field 1116. Alternatively, each of the fields illustrated in FIG. 11B may expand into user-input fields, into database lists of available data, and the like, depending on the specific application.

Figure 11C:
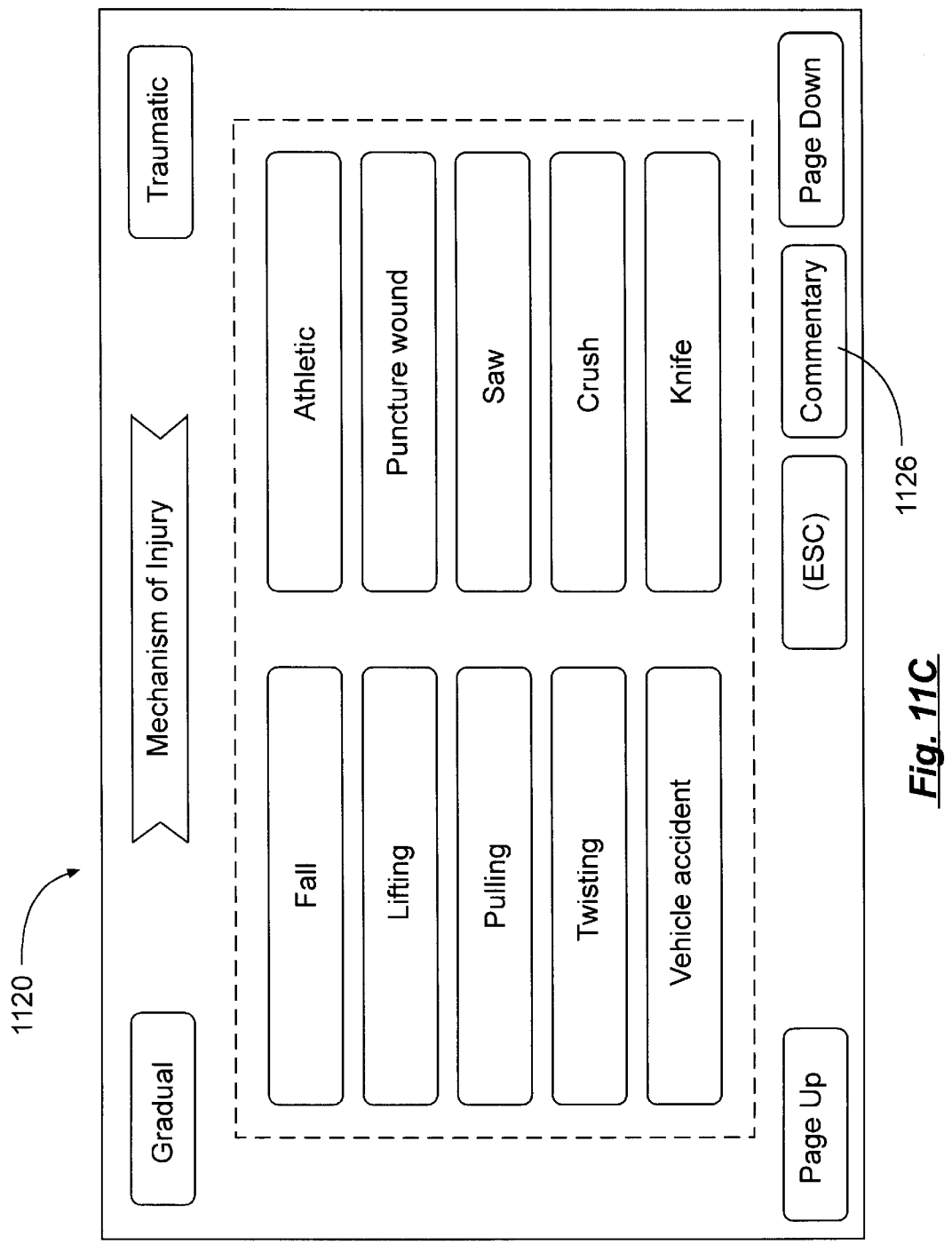
FIG. 11C is a graphical representation of a Mechanism of Injury menu of the embodiment of the invention shown in FIG. 11A.

Similarly, the "Mechanism of Injury" field 1120 may present the user with multiple sub-fields to select. Preferably, the user is presented with two categories describing the mechanism of injury: gradual and traumatic. Each of these categories preferably has a separate sub-menu presenting data appropriate for the selected field. An example of a sub-menu for a traumatic "Mechanism of Injury" 1120 is illustrated in FIG. 11C.

In a preferred embodiment, activation of the "Description of Symptoms" field 1118 will display a menu of generic categories of observed pathologies. For example, the descriptions may include: wound/scar; edema/inflation; vascular/lymphatic; pain/hypersensitivity/autonomic phenomena; nerve/sensibility; muscle/myotendon unit/tendon; posture/breathing patterns; ROM deficiency; praxis/ coordination; strength/endurance; and the like. These particular fields will change based on the particular application.

In a similar manner, the "Accident Location" field 1122 displays a menu of common locations of the onset of present illness. For example, the menu may include the fields of: work; non-work related; hobby; home; or other.

Several of these menus, such as "Location of Symptoms" 1116, "Description of Symptoms" 1118, "Mechanism of Injury" 1120, and "Accident Location" 1124, may include a "Commentary" button 1126. This button may be used by the user to access a text field that enables the user to directly enter text comments relating to the particular menu.

The other menus presented in the Present Illness menu 912 may either be direct data entry fields, linked to the database, or other fields or buttons of the type described above.

The Past Medical History menu 914 is used to record various patient historical information relating to the present illness. For example, and as shown in FIG. 9A, the Past Medical History menu 914 may include a "previous treatments" field 920 by which the user, by any of the methods described in detail above, may enter historical data relating to the particular patient's previous treatments for the present illness or injury. The "Previous Treatments" field 920 may be used to access a menu listing categories of treatment, such as rehabilitation, splint, brace, strengthening, surgery, and the like, each of which may be linked to a data base for a listing of specific treatments within each category. In alternative embodiments, this field 920 may be used to enter any type of historical customer or vendor data that may be relevant to a present transaction.

Figure 12:
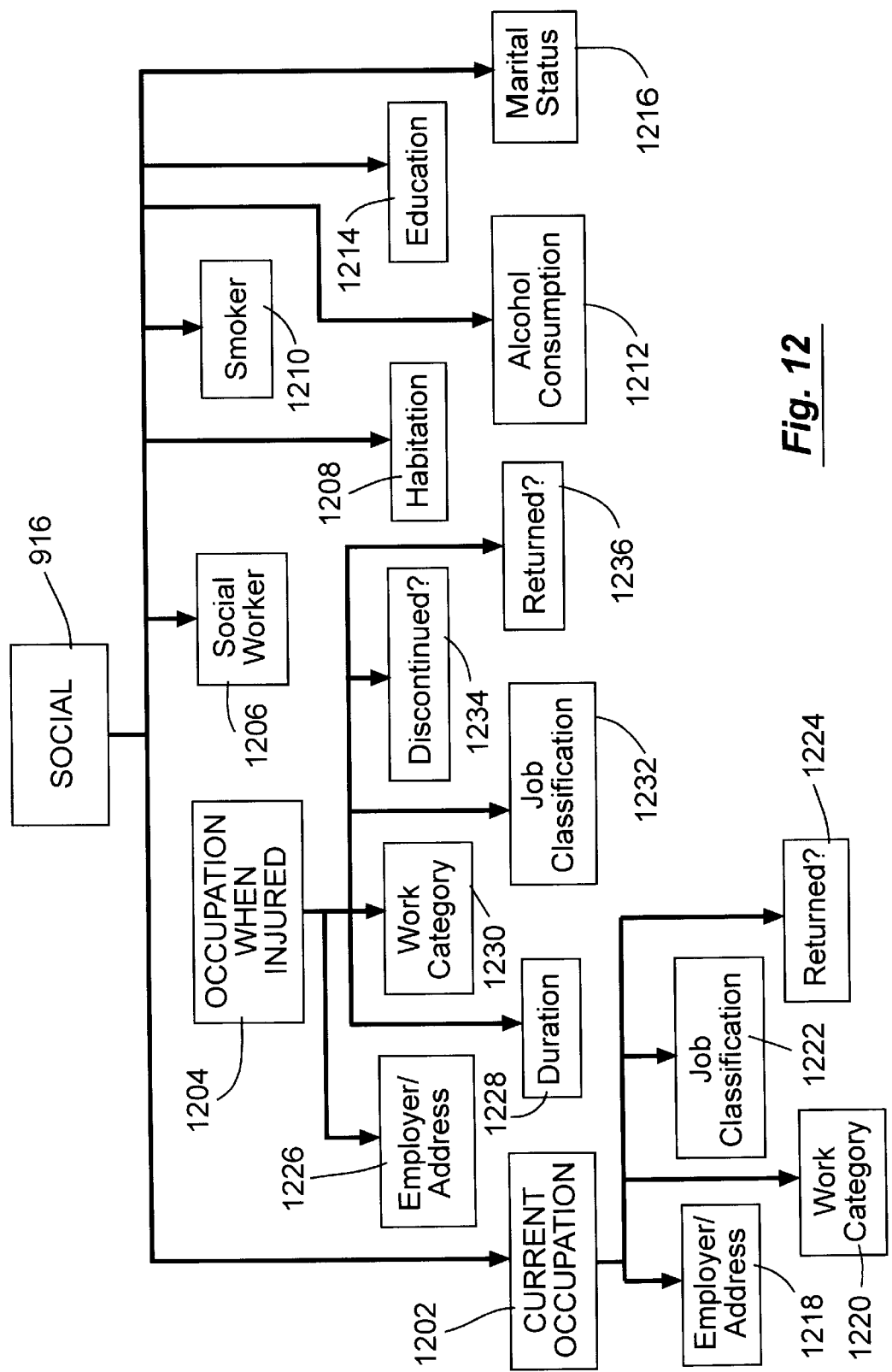
FIG. 12 is a hierarchical chart of the Social menu of an embodiment of the present invention.

The Social menu 916 allows the entry of occupational and social-behavior data. For example, employment history as it relates to the present illness, may be entered using employer demographic menus and lists linked to the database. A preferred example of sub-menus contained in a Social menu 916 is shown in FIG. 12.

In the illustrated embodiment, the Social menu 916 preferably consists of a set of sub-menus, including Current Occupation 1202 and Occupation when Injured 1204, as well as fields for entering data, including: "Social Worker" associated with the patient 1206; "Habitation" 1208; "Smoker" 1210; "Alcohol Consumption" 1212; "Education" 1214; and "Marital Status" 1216; among others. Each of these fields relate to information relevant to the patient's present illness. For example, the name and demographics of the social worker involved with the patient is entered in the "Social Worker" field 1206. This field 1206 may be linked in a manner similar to the "Primary Physician" field 1016, described above. Additional fields may be added, as appropriate, to collect and record social behavior of the patient as relevant to the present illness.

The Current Occupation menu 1202 may be used to record employer information, such as employer name, address, phone numbers, and contact personnel information in an employer sub-menu 1218. In addition, the menu 1202 preferably includes a "Work Category" field 1220 for recording the particular work category, such as assembly, athlete, carpenter, clerical, laborer (light), laborer (heavy), maintenance, professional, retired, and the like. A user may enter each of these categories into the "Work Category" field 1220 by selecting a presented category. Alternatively, the categories may be called from the database upon user selection of the particular field, or the field may remain as a manual entry field, depending on the particular application.

Similarly, a "Job Classification" field 1222 may be included in the Current Occupation sub-menu 1202, for providing a job classification menu relevant to job-related injuries. A "Returned" field 1224 may be used to indicate the date on which the patient returned to his/her current occupation.

The Occupation When Injured submenu 1204 relates to information regarding the patient's activities at the time of injury, as contrasted with the current occupation of the patient. That sub-menu 1204 includes fields for entering information regarding: information on the employer at the time of injury 1226; the duration at the job prior to injury 1228; "Work Category" 1230; "Job Classification" 1232; whether the patient's job was discontinued due to the injury 1234; and whether the patient returned to the same type of job 1236. The fields for "Employer" 1226, "Work Category" 1230, and "Job Classification" 1232 preferably are functionally similar to the corresponding files in the Current Occupation menu 1202.

The "Discontinued" field 1234 is for entering data concerning whether the patient's job was interrupted by the injury. If the patient's job was discontinued, the user may then enter the date that the job was discontinued. The "Returned" field 1236 relates to whether or not the patient returned to the same type of work, as compared with the similar "Returned" field 1224 found in the Current Occupation menu 1202, which field relates to whether or not the patient returned to any work.

The Text Paragraphs menu 918 that allows a user to enter relatively arbitrary, unstructured text relating to the patient. In a preferred embodiment, this menu 918 includes a number of buttons and fields that contain pre-programmed subject titles. An example of such a Text Paragraphs menu 918 is illustrated in FIG. 9B.

Once a user has proceeded through all of the sub-menu and fields as appropriate via the New Patient menu 904, the input data resides in the database 114.

Figure 13:
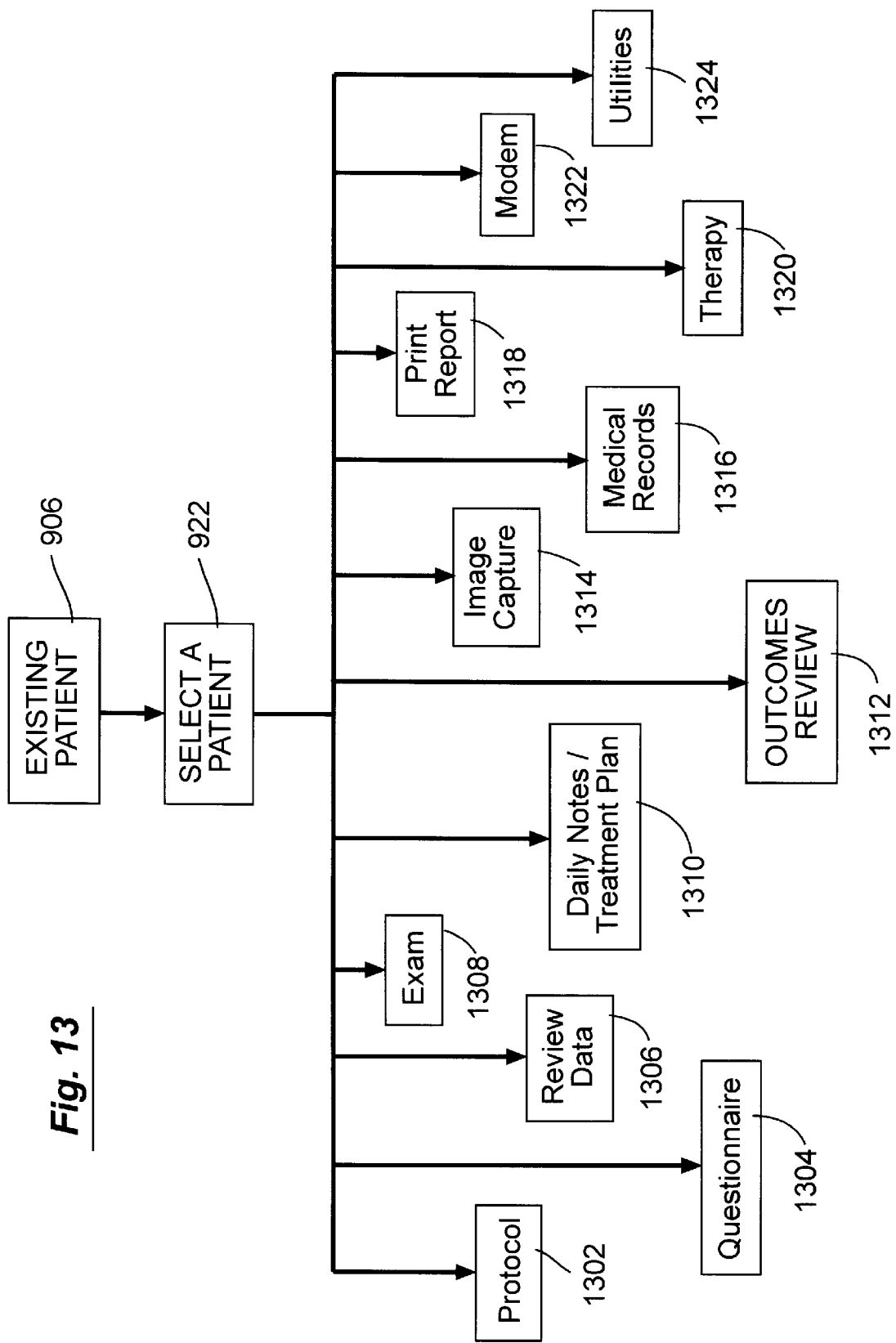
FIG. 13 is a hierarchical chart of the Existing Patient menu of an embodiment of the present invention.

In practicing the present invention, an outcomes profile report of the type described above may be generate by instructions input from the user through the Existing Patient menu 906. As shown in FIG. 13, once the user selects a patient from the database using the Select a Patient menu 922, the user is presented with a menu containing multiple menus, including: Protocol 1302, through which a user may select and perform standard or custom protocols, which may be protocols previously performed on the current patient, and through which a user may modify a protocol to be performed; Questionnaire 1304, through which a user may select a questionnaire for the user and/or patient to answer, as described in further detail below in connection with FIG. 16A; Review Data 1306, which reviews one or more exams from data files for the current patient, and through which a user may revise physical exam data and enter narrative; Exam 1308, through which a user selects exams or exercises to be performed; Daily Notes/Treatment Plan 1310, through which a user may enter narrative or CPT data; Outcomes Review, or Outcomes Profile Report 1312, as discussed above in detail; Image Capture 1314, which utilizes an image capture subsystem that may be used in conjunction with the present system, and which is generally commercially available and known to those skilled in the relevant art; Medical Records 1316, through which a user may enter demographics and other narrative and through which a user may record facts which may be used for sorting in the outcomes profile management report function; Print Report 1318, through which a user may print single data or comparison reports, as requested by the user; Therapy 1320, through which a user may perform exercises and dynamic muscle tests; Modem 1322, which sends Dexter™ formatted data to another Dexter™ system and examines similar data received from other Dexter™ system Utilities 1324, an example of which is illustrated in detail in FIG. 15. In alternative embodiments, these menus may be adapted and the number of menus may vary to suit the particular application.

Figure 14:
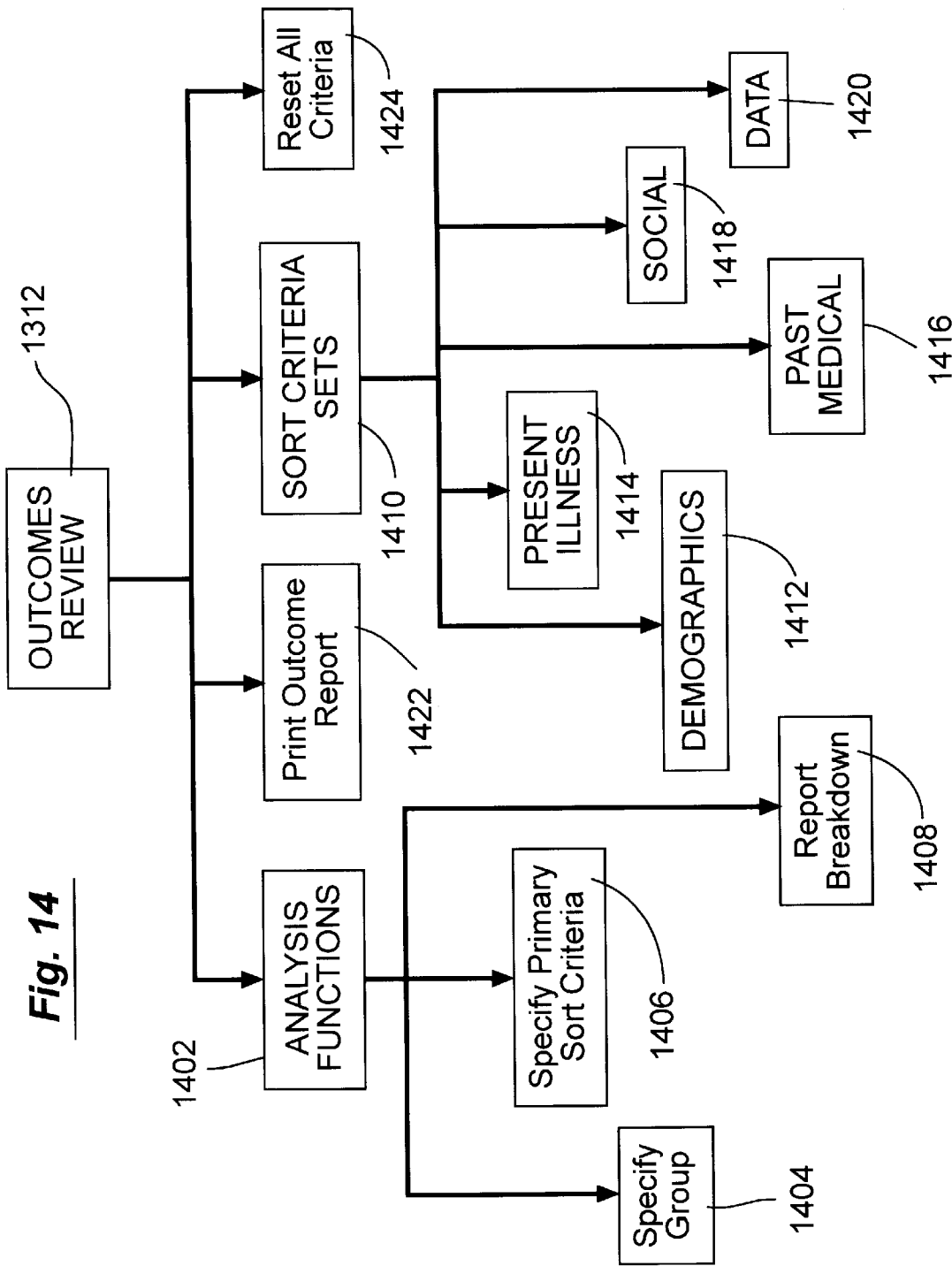
FIG. 14 is a hierarchical chart of the Outcomes Review menu of an embodiment of the present invention.

The Outcomes Review menu 1312 is most significant in practicing the present invention, and is shown in further detail in FIG. 14. The Outcomes Review menu 1312 includes a series of sub-menus corresponding to the functions described above in connection with FIGS. 3 and 6A–6D. FIG. 5 shows a Basic Window 500 that corresponds to an outcomes review menu 1312. FIG. 13 shows the hierarchical display for such the menus associated with the Outcomes Review menu 1312. The Outcomes Review menu 1312 includes a display of Analysis Functions menus 1402 which enable the user to select an analysis function from among Specify Group 1404, Specify Primary Sort Criteria 1406, and Report Breakdown 1408. The Outcomes Review menu 1312 also includes a display of sort criteria sets menus 1410 that may be used to select a sort criteria set from a Demographics menu 1412, a Present illness menu 1414, a Past Medical menu 1416, a Social menu 1418, and a Data menu 1420.

Each of these sort criteria set menus 1410 have corresponding subset fields which are displayed in the menu corresponding to the selected sort criteria set menu 1410. For example, the Demographics menu 1412 preferably includes buttons corresponding to sort criteria subset fields of: type of insurance; payer; language; ethnicity; gender; age; primary physician; referral physician; clinician/physical therapist; rehabilitation nurse; other related party; and clinic name. Note that the data corresponding to each of these sort criteria subset fields was entered, if at all, during the activation of the New Patient menu 904 and corresponding submenus.

Upon selecting or indicating a particular sort criteria in the subset fields, the system searches the database for records containing the user-selected data in the user-selected field. For example, a user may, beginning with the Outcomes Review menu 1312, select the Sort Criteria menu 1410, then select from that menu 1410 the Demographics menu 1412, and then select the "primary physician" field. At that point, the user either may enter the name of a primary physician or, in a preferred embodiment, select a primary physician from a list generated from the database by activating the primary physician field. Upon generating an outcomes report in accordance with the present invention, the CPU 102 engages a sort function that identifies the records in the database containing the selected primary physician in the field labelled "primary physician". That record becomes one of the selected records that form the group of patients against which an analysis is performed, as described in detail above.

In a preferred embodiment, the Present Illness 1414 menu includes the fields of: patient discharged?; location of symptoms; diagnosis code; description of symptoms; mechanism of injury; and accident location, among others. The Past Medical menu 1416 includes the field of previous treatments, among others. In a preferred embodiment, the Social menu 1418 preferably includes parameters such as: smoker; alcohol consumption; education; marital status; returned to work?; employer when injured; returned to same type of work?; work category; social worker associated wit the patient; job classification; habitation; and work discontinued due to injury?, among others. The Data menu 1420 preferably includes two fields: treatment plan and questionnaire statistics. The data for these fields also is entered during a user's use of the New Patient menu 904.

The Outcomes Review menu 1312 also includes, in a preferred embodiment, a Print Outcomes Report menu 1422 for initiating a print function as described above in connection with FIG. 5. The Outcomes Review menu 1312 also may include a "reset all criteria" field 1424 for resetting all sort criteria prior to executing the outcomes review report.

In a preferred embodiment, the Home Menu 200 includes a Utilities menu 908. That menu 908 may be used to access buttons for activating certain functions to be performed outside of the data input and outcomes report generation. In the illustrated example of FIG. 15, the Utilities menu 908 includes displays of buttons for: "Computer Setup" 1502; "Calibration" 1504; "Voice Utilities" 1506; "Purge Utilities" 1508; data archival and retrieval 1510; exiting to the DOS shell 1512; and setting date and time 1514. Other buttons may be added, depending on the particular hardware environment and the specific application.

Figure 15:
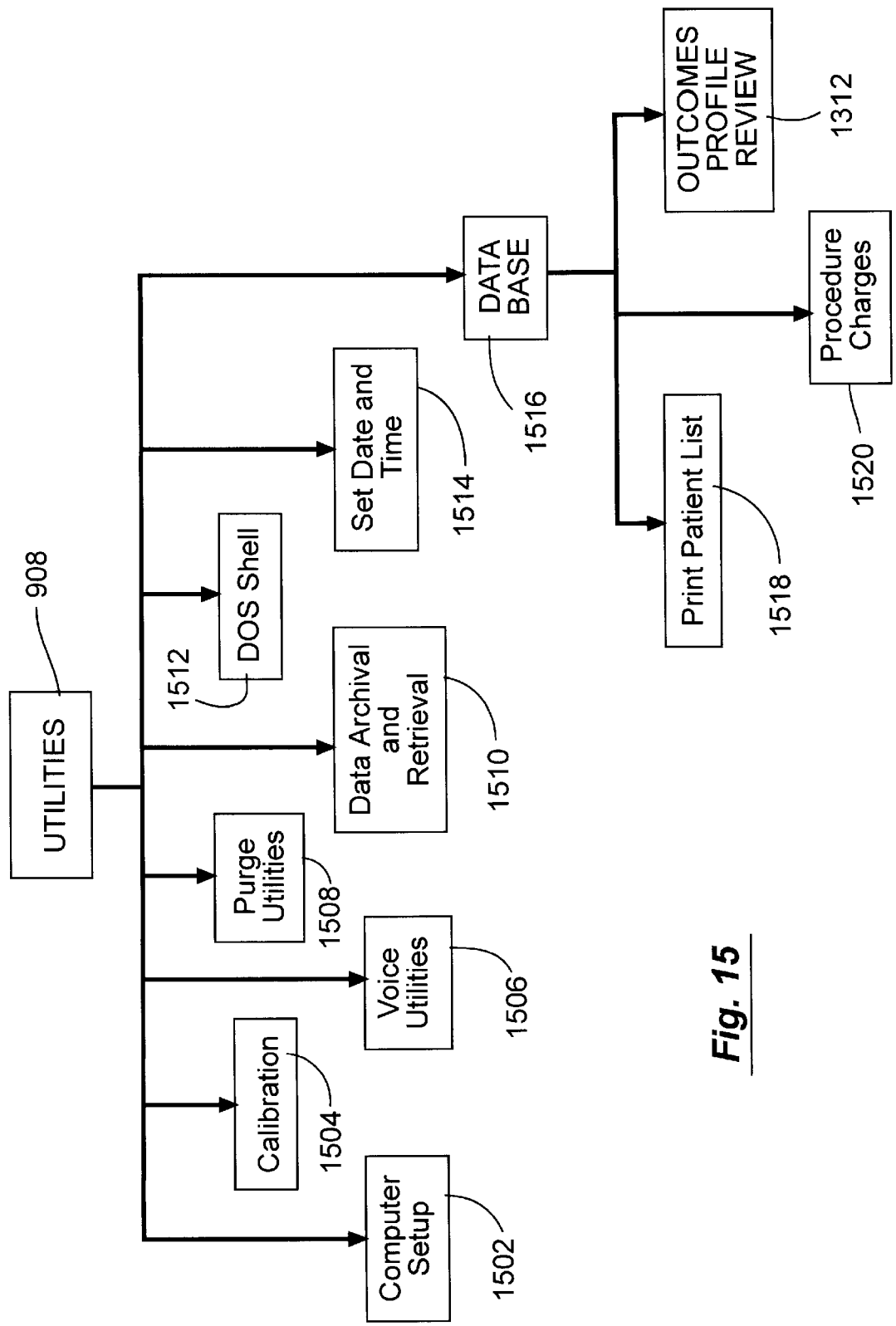
FIG. 15 is a hierarchical chart of the Utilities menu of an embodiment of the present invention.

Also in the illustrated embodiment of FIG. 15, the Utilities menu 908 includes a Database menu 1516, for accessing and performing functions related to the database. In addition to miscellaneous buttons, such as "Print Patient List" 1518 and "Procedure Change" 1520, the menu 1516 may include an alternative access to the Outcome Profile Review menu 1312. Alternate pathways to various ones of the functions may readily be designed into the present system.

Figure 16:
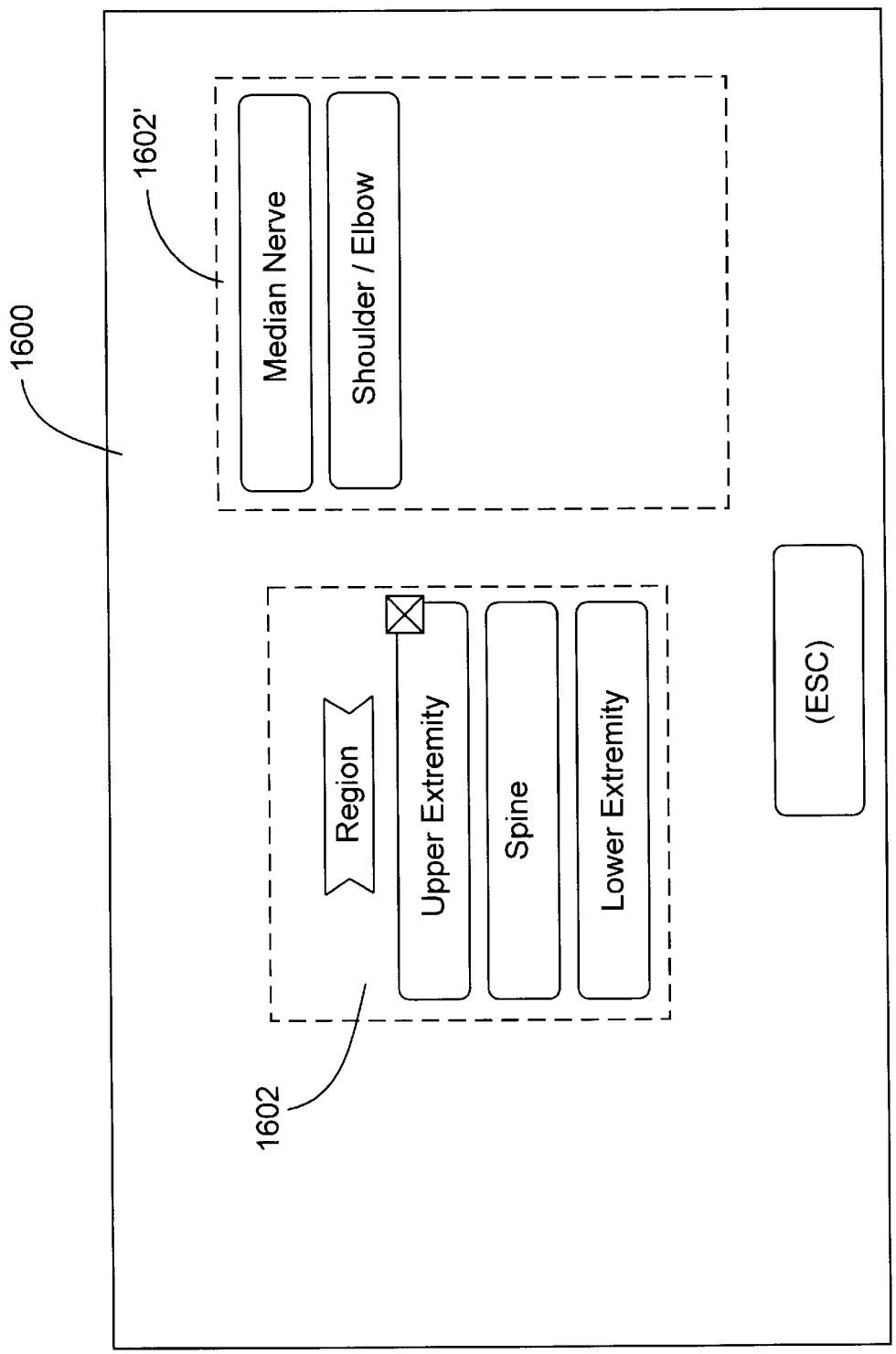
FIG. 16 is a graphical representation of a Current Upper Extremity menu of the Questionnaire function of the embodiment of the invention shown in FIG. 13.

Returning to FIG. 13, a user may enter the Questionnaire function 1304 of the Existing Patient menu 906 to begin a patient interface for entering patient data relating to functional status of the patient, symptom severity for that patient, and satisfaction by the patient of past treatment received. In a preferred embodiment, a user is presented with a hierarchical display of menus that present various questions relating to general patient condition. FIG. 16 shows an example of a menu 1600 that may be displayed on the display device 104. In the illustrated example, a current upper extremity questionnaire is presented to a user. As illustrated, the user may enter "region" data in the Region field 1602 by indicating whether the region of the patient's symptoms are occurring in the upper extremity, the spine, or in the lower extremity. The "region" data may be presented in a single Region field 1602 or split among several fields 1602', as illustrated.

In a preferred, clinical environment of practicing the present invention, the user/clinician is presented with a series of such preliminary questionnaires that enter certain, high-level information about a particular patient's symptoms. Once the clinician has entered all data via this first set of menus, then the system begins to present a series patient data screens.

In a preferred embodiment, the questionnaires are selected by the clinical staff and are both general health and pathology specific. Once selected, the new patient preferably is provided with a tutorial on what is expected in responding to the questions presented in the series of patient menus. After the tutorial, the patient is serially and dynamically presented with a series of menus, each of which presents the patient, in a very preferred embodiment, with a series of active touch screen buttons. With the display of each patient question, the response button changes verbiage so as to correspond to the question being displayed. As the patient makes a selection, the response is recorded by the CPU 102 and stored in the database, and the next menu presenting the next question of the series is brought up to the display device 104. In some instances, the succeeding questions are dependent upon the response of the patient to the preceding question.

In a preferred embodiment, the patient's responses to each presented question are weighted and scored so that categories of client perspectives, i.e., the perspective a client has on his or her condition, can be scored and a trend analysis performed. Such categories preferably cover the topics of functional status, symptom severity, and patient satisfaction with the treatment and services delivered by the particular clinic and/or physician. These scores preferably are bundled together with procedure costs and clinic visit data to arrive at an assessment of the effectiveness of specific procedure plans and treatments.

Figure 17:
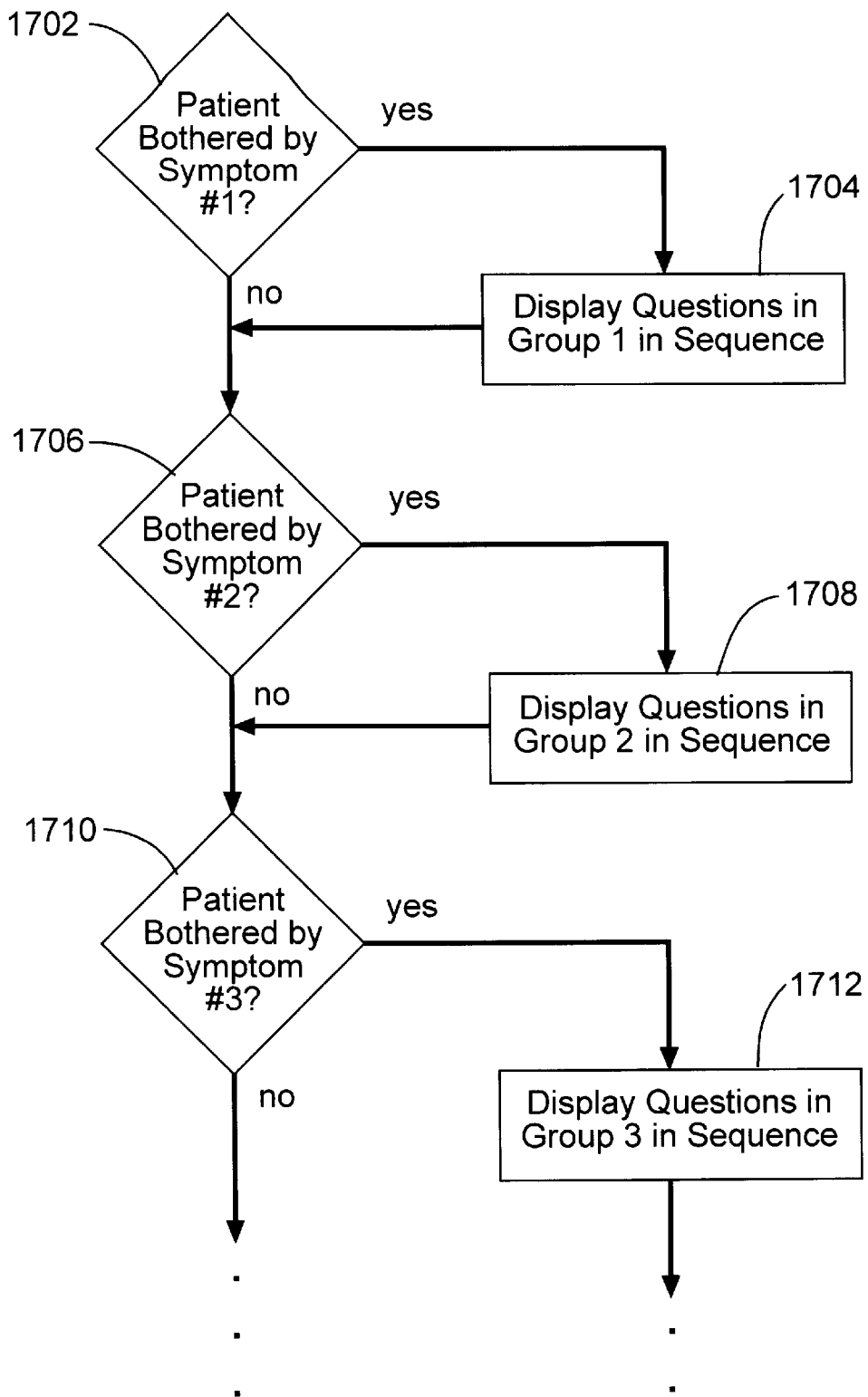
FIG. 17 is a hierarchical chart of questions that may be displayed to a patient/user as part of the Questionnaire function of an embodiment of the present invention.

A functional flow chart of such a series of patient data screens is shown in FIG. 17. In that illustrated flow chart, the system presents a series of menus to the patient, each of which inquires into certain predetermined symptoms and is intended to be answered directly by the patient and not by the clinician.

As illustrated in FIG. 17, the system first queries 1702 whether the patient is bothered by symptom #1. The specific, predetermined symptom preferably is derived from the answer to the preliminary set of questionnaires answered by the clinician, as described above. An affirmative answer to the query 1702 results in the display 1704 of a set of additional and specific questions relating to the particular symptom. Thus, a patient questionnaire may dynamically present different groups of specific questions 1706, 1710 based on input from the patient, and each of which result in the display 1708, 1712 of specific related questions. For example, FIG. 18A is a graphical illustration of a menu presented to a patient. An affirmative response (i.e., "occasionally", "less than once a day", "once a day", or "more than once a day") results in the presentation of the menu shown in FIG. 18B, with a related question.

The patient questionnaire sequence may be used to obtain basic medical history information regarding a patient, input directly by the patient. A graphical illustration of such a menu that may be presented to a patient is shown in FIG. 18C. While sitting in the reception room of a clinic or hospital, the patient may interact with the present system to complete a medical history, by answering questions such as those presented the illustrated menu of FIG. 18C. The patient response to the menus are input directly into the system database for subsequent retrieval and use in performing certain statistical and trend analyses.

The use of interactive patient questionnaires of the type described herein also may be used to input data over a period of time. For example, turning to the graphical illustration of a menu in FIG. 18D, the patient may directly provide information regarding symptom severity of a present illness. The patient may answer the same question a number of times during sequential clinic visits and over the course of treatments to provide data that may be used to identify a trend of improvement, a plateau in improvement, or otherwise.

In a preferred embodiment, the patient's response to subjective questions, such as "In the past week, how often have you suffered weakness in arm and/or hand", with subjective responses, such as "a little of the time" or "some of the time", as shown in FIG. 18D, is scored to obtain a quantitative score. The scores may be grouped according to certain published criteria to identify trends and statistical probabilities, as appropriate.

In a preferred embodiment, the patient questionnaire function of the present system includes menus presenting questions regarding the functional status of a patient, such as the menu shown in FIG. 18E. The patient's response to such questions preferably are scored and used to perform a trend analysis of the functional aspects of a present illness over time.

Other patient questionnaire menus may present questions regarding the severity of a particular symptom. An example of such a menu is shown in FIG. 18F. By scoring a patient's answer to such questions, trends in symptom improvement may be identified. Analyses of such data also may be used to determine whether a particular treatment or therapy is having an affect on a particular symptom for the specific patient. Early detection of non-improvement potentially enables a treating physician or physical therapist to change treatment before the symptom is aggravated.

An additional aspect of a preferred embodiment of the patient questionnaire function of the present system is to track quality assurance issues with the patient. As shown in the example of FIG. 18G, the patient may be presented with a menu presenting a quality assurance question, such as "how satisfied are you with your treatment?" By scoring the qualitative responses to such questions, a treating physician or clinic may quantitate patient satisfaction and modify a particular treatment or environmental factor that contributes to the patient's satisfaction.

The Questionnaire function 1304 may include a set of menus presenting questions that are responded to by the clinical staff. An example of such a menu is shown in FIG. 18H. By using such questionnaires, a standard protocol of evaluation of every new patient can be followed. Because there is a high interest among the insurance and healthcare industries of having clinicians review and treat symptoms in a uniform fashion, such standardized follow-up questions are highly desirable in an embodiment of the present invention that is used in a clinical environment. Outside the healthcare environment, the need for such follow-up is equally compelling, such as in a sales/marketing environment in which standardized follow-up most likely directly results in improved sales numbers.

The questions presented in the menus described above may be licensed from any one or more of a variety of questionnaires currently available. The correlations between symptoms and questions presented to the patient may be derived from technical journals, independent clinical evaluations, and the like. The number of menus and questions per questionnaire may vary depending on the particular application and symptom.

The functions of the system described above in detail ay be stored as computer software on a computer usable medium magnetically, electrically, or optically. Specifically, the media may be in the form of magnetic diskettes, magnetic tapes, optical disks, Read Only Memory (ROM), Direct Access Storage Devices, and the like for use with various computer hardware systems. Such computer program products may be devised, made, and used as a component part of a machine utilizing optics, magnetic properties, and/or electronics to perform the functions described herein and contained in computer program form thereon.

Depending on the size of the system software, various compressions algorithms may be used in conjunction with the disclosed system for storage and retrieval on such storage medium, or the system software may be serially stored across multiple media for subsequent installation and use in conjunction with particular hardware configurations, as appropriate for the particular application.

Although a preferred embodiment is shown and described above, it should be understood that the invention may be embodied in other specific forms without departing from the spirit or essential characteristics thereof. The present embodiment are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A computer based method for evaluating treatment effectiveness comprising:

storing group data in a database, the group data comprising demographic information about a plurality patients;

presenting to a patient a first questionnaire, said first questionnaire having at least one of a plurality of questions regarding quality of life;

receiving from the patient a first set of responses to the first questionnaire, said first set of responses providing a first indication of quality of life of said patient;

performing statistical analysis on the first set of patient responses and the group data in the database, to produce a first profile characterizing the effectiveness of treatment received by the patient, said effectiveness of treatment based upon said first indication of quality of life of said patient;

presenting a second questionnaire to the patient at a later time than said first questionnaire, said second questionnaire having at least one of said plurality of questions regarding quality of life;

receiving from the patient a second set of responses to the second questionnaire, said second set of responses providing a second indication of quality of life of said patient; and performing statistical analysis on the second set of patient responses and the group data, in the database, to produce a second profile characterizing the effectiveness of treatment received by the patient.

2. The method of claim 1 wherein the statistical analysis further comprises computing a statistical average.

3. The method of claim 1 wherein the statistical analysis further comprises computing a statistical deviation.

4. The method of claim 1 wherein the questionnaire is presented to the patient on a display screen coupled to a computer using a hierarchical arrangement of menus.

5. The method of claim 1 wherein the first questionnaire and the first profile are displayed to the patient on a display screen.

6. The method of claim 1 further comprising the step of printing the first profile.

7. The method of claim 1, further comprising performing computation on the first profile and the second profile to produce a difference profile, said difference profile characterizing an effectiveness of treatment based upon a difference between said first and said second indications of quality of life of said patient.

8. A computer based method for evaluating treatment impact on sociological factors comprising:

storing group data in a database, the group data comprising information about a plurality of patients;

present to a patient a first questionnaire, said first questionnaire having at least one of a plurality of questions regarding quality of life;

receiving from the patient a first set of responses to the fist questionnaire, said first set of responses providing a first indication of quality of life of said patient based upon said sociological factors;

performing statistical analysis on the first set of patient responses and the group data in the database, to produce a first profile character the impact of treatment on the social behavior patterns of the patient, based upon said first indication of quality of life of said patient based upon said sociological factors;

presenting a second questionnaire to the patient at a later time than said first questionnaire, said second questionnaire having at least one of said plurality of questions regarding quality of life;

receiving from the patient a second set of responses to the second questionnaire, said second set of responses providing a second indication of quality of life of said patient based upon said sociological factors; and performing statistical analysis on the second set of patient responses and the group data, in the database, to produce a second profile characterizing impact of treatment on the social activities of the patient.

9. The method of claim 8 wherein the statistical analysis further comprises computing a statistical average.

10. The method of claim 8 wherein the statistical analysis further comprises computing a statistical deviation.

11. The method of claim 8 wherein the questionnaire is presented to the patient on a display screen coupled to a computer using a hierarchical arrangement of menus.

12. The method of claim 8 wherein the first questionnaire and the first profile are displayed to the patient on a display screen.

13. The method of claim 8 further comprising the step of printing the profile.

14. The method of claim 8, further comprising performing computation on the first profile and the second profile to produce a difference profile, said difference profile characterizing an effectiveness of treatment based upon a difference between said first and said second indications of quality of life of said patient.

15. A computer based method for determining an outcomes profile, said outcomes profile comprising demographic, quality of life and treatment effectiveness information for a medical institution, said method comprising:

storing group data in a database, the group data containing information about a plurality of patients;

presenting to a patient a first questionnaire, said first questionnaire having at least one of a plurality of questions about quality of life and demographic information about the patient;

receiving from the patient a first set of responses to the first questionnaire, said first set of responses providing a first indication of quality of life of said patient;

performing statistical analysis on the first set of patient responses and the group data in the database, to produce said outcomes profile, wherein said outcomes profile provides an indication of effectiveness of treatment, said indication of effectiveness of treatment based upon said first indication of quality of life of said patient;

presenting a second questionnaire to the patient at a later time than said first questionnaire, said second questionnaire having at least one of said plurality of questions regarding quality of life and demographic information;

receiving from the patient a second set of responses to the second questionnaire, said second set of responses providing a second indication of quality of life of said patient; and performing statistical analysis on the second set of patient responses and the group data, in the database, to produce a second outcomes profile, wherein said second outcomes profile provides an indication of effectiveness of treatment, said indication of effectiveness of treatment based upon said second indication of quality of life of said patient.

16. The method of claim 15 wherein the statistical analysis further comprises computing a statistical average.

17. The method of claim 15 wherein the statistical analysis further comprises computing a statistical deviation.

18. The method of claim 15 wherein the first and second questionnaires are presented to the patient on a display screen coupled to a computer using a hierarchical arrangement of menus.

19. The method of claim 15 wherein the first questionnaire and the outcomes profile are displayed to the patient on a display screen.

20. The method of claim 15 wherein the second questionnaire and the second outcomes profile are displayed to the patient on a display screen.

21. The method of claim 15 further comprising the step of printing the outcomes profile.

22. The method of claim 15 further comprising performing computation on the outcomes profile and the second outcomes profile to produce a difference profile, said difference profile characterizing an effectiveness of treatment based upon a difference between said first and said second indications of quality of life of said patient.

* * * * *

UNITED STATES PATENT AND TRADEMARK OFFICE
CERTIFICATE OF CORRECTION

PATENT NO. : 6,177,940 B1
DATED : January 23, 2001
INVENTOR(S) : Malcolm L. Bond and Bruce Richard Chapman It is certified that error appears in the above-identified patent and that said Letters Patent is hereby corrected as shown below:

Column 20,
Lines 7-10:
    1. A computer based method for evaluating treatment effectiveness comprising:
    storing group data in a database, the group data comprising demographic information about a plurality of patients;
Lines 59-61:
    presenting [present] to a patient a first questionnaire, said first questionnaire having at least one of a plurality of questions regarding quality of life;

Column 20-21,
Line 66 through line 4:
    performing statistical analysis on the first set of patient responses and the group data in the database, to produce a first profile characterizing [character] the impact of treatment on the social behavior patterns of the patient, based upon said first indication of quality of life of said patient based upon said sociological factors;

Signed and Sealed this

Thirteenth Day of November, 2001

*Attest:*

*Attesting Officer*

NICHOLAS P. GODICI
*Acting Director of the United States Patent and Trademark Office*